(12) United States Patent
Brandt et al.

(10) Patent No.: US 8,088,903 B2
(45) Date of Patent: Jan. 3, 2012

(54) FLEA HEAD, NERVE CORD, HINDGUT AND MALPIGHIAN TUBULE NUCLEIC ACID MOLECULES, PROTEINS AND USES THEREOF

(75) Inventors: Kevin S. Brandt, Fort Collins, CO (US); Patrick J. Gaines, Fort Collins, CO (US); Dan T. Stinchcomb, Fort Collins, CO (US); Nancy Wisnewski, Fort Collins, CO (US)

(73) Assignee: Heska Corporation, Loveland, CO (US)

( * ) Notice: Subject to any disclaimer, the term of this patent is extended or adjusted under 35 U.S.C. 154(b) by 698 days.

(21) Appl. No.: 11/565,729

(22) Filed: Dec. 1, 2006

(65) Prior Publication Data

US 2007/0270576 A1  Nov. 22, 2007

Related U.S. Application Data

(63) Continuation of application No. 10/621,901, filed on Jul. 16, 2003, now abandoned.

(60) Provisional application No. 60/319,414, filed on Jul. 22, 2002.

(51) Int. Cl.
    *C07H 21/02* (2006.01)
    *C07H 21/04* (2006.01)
(52) U.S. Cl. ............... 536/23.1; 536/23.5; 536/24.31
(58) Field of Classification Search ................. None
    See application file for complete search history.

(56) References Cited

FOREIGN PATENT DOCUMENTS
WO    WO 00/61621    10/2000

OTHER PUBLICATIONS

Metzler et all Solution structure of human CTLA-4 and delineation of a CD80/CD86 binding site conserved in CD28.° Nature Structural Biol. 4:527-531, 1997.*
Smith et al. The challenges of genome sequence annotation or "the devil is in the details". Nat. Biotech.15:1222-1223, 1997.*
Brenner S. 'Errors in genome annotation.' Trends in Genetics 15:132-133, 1999.*
Bowie et al. Decipering the Message in Protein Sequences: Tolerance to Amino Acid Substitutions. Science 247:1306-1310, 1990.*
Lerner et al. 'Tapping the immunological repertoire to produce antibodies of predetermined specificity.' Nature. 299:593-596, 1982.*

\* cited by examiner

*Primary Examiner* — Nora Rooney
(74) *Attorney, Agent, or Firm* — Sheridan Ross P.C.

(57) ABSTRACT

The present invention relates to flea head, nerve cord, hindgut and Malpighian tubule proteins; to flea head, nerve cord, hindgut and Malpighian tubule nucleic acid molecules, including those that encode such flea head, nerve cord, hindgut and Malpighian tubule proteins; to antibodies raised against such flea head, nerve cord, hindgut and Malpighian tubule proteins; and to compounds that inhibit flea head, nerve cord, hindgut and Malpighian tubule protein activity. The present invention also includes methods to obtain such proteins, nucleic acid molecules, antibodies, and inhibitory compounds. Also included in the present invention are therapeutic compositions comprising proteins, nucleic acid molecules, antibodies, or protective compounds derived from proteins of the present invention as well as the use of such therapeutic compositions to protect animals from flea infestation. Also included in the present invention is the use of flea head, nerve cord, hindgut and Malpighian tubule proteins to derive inhibitory compounds.

3 Claims, No Drawings

FLEA HEAD, NERVE CORD, HINDGUT AND MALPIGHIAN TUBULE NUCLEIC ACID MOLECULES, PROTEINS AND USES THEREOF

CROSS-REFERENCE TO RELATED APPLICATIONS

This application is a Continuation of U.S. patent Ser. No. 10/621,901, filed Jul. 16, 2003, now abandoned; which claims priority to U.S. Provisional Application Ser. No. 60/319,414, filed Jul. 22, 2002, both of which are entitled "FLEA HEAD, NERVE CORD, HINDGUT MALPHIGIAN TUBULE NUCLEIC ACID MOLECULES, PROTEINS AND USES THEREOF," and incorporated herein by reference in their entirety.

FIELD OF THE INVENTION

The present invention relates to nucleic acid molecules isolated from the head and nerve cord of a flea, nucleic acid molecules isolated from the hindgut and Malpighian tubule of a flea, proteins encoded by such nucleic acid molecules, antibodies raised against such proteins, and inhibitors of such proteins. The present invention also includes therapeutic compositions comprising such nucleic acid molecules, proteins, antibodies, and/or other inhibitors, as well as uses thereof.

BACKGROUND OF THE INVENTION

Flea infestation of animals is a health and economic concern to pet owners. In particular, the bites of fleas are a problem for animals maintained as pets because the infestation becomes a source of annoyance not only for the pet but also for the pet owner who may find his or her home generally contaminated with insects. Fleas are known to directly cause a variety of diseases, including allergies, and also carry a variety of infectious agents including, but not limited to, endoparasites (e.g., nematodes, cestodes, trematodes and protozoa), bacteria and viruses. As such, fleas are a problem not only when they are on an animal but also when they are in the general environment of the animal.

Bites from fleas are a particular problem on many animals because they can cause a hypersensitive response in animals which is manifested as disease. For example, bites from fleas can cause an allergic disease called flea allergic (or allergy) dermatitis (FAD). A hypersensitive response in animals typically results in localized tissue inflammation and damage, causing substantial discomfort to the animal.

The medical importance of flea infestation has prompted the development of reagents capable of controlling flea infestation. Commonly encountered methods to control flea infestation are generally focused on use of insecticides, which are often unsuccessful for one or more of the following reasons: (1) failure of owner compliance (frequent administration is required); (2) behavioral or physiological intolerance of the pet to the pesticide product or means of administration; and (3) the emergence of flea populations resistant to the prescribed dose of pesticide.

Thus, there remains a need to develop a reagent and a method to protect animals from flea infestation.

SUMMARY OF THE INVENTION

The present invention relates to a novel product and process for protection of animals from flea infestation.

The present invention provides flea head and nerve cord (HNC) proteins and flea hindgut and Malpighian tubule (HMT) proteins; nucleic acid molecules encoding flea HNC proteins and flea HMT proteins; antibodies raised against such proteins (i.e., anti-flea HNC antibodies and anti-flea HMT antibodies respectively); mimetopes of such proteins or antibodies; and compounds that inhibit flea HNC or HMT activity (i.e., inhibitory compounds or inhibitors).

The present invention also includes methods to obtain such proteins, mimetopes, nucleic acid molecules, antibodies and inhibitory compounds. The present invention also includes the use of proteins and antibodies to identify such inhibitory compounds as well as assay kits to identify such inhibitory compounds. Also included in the present invention are therapeutic compositions comprising proteins, mimetopes, nucleic acid molecules, antibodies and inhibitory compounds of the present invention including protective compounds derived from a protein of the present invention that inhibit the activity of HNC and/or HMT proteins; also included are uses of such therapeutic compounds to reduce flea infestation.

One embodiment of the present invention is an isolated nucleic acid molecule that hybridizes with a nucleic acid molecule selected from the group consisting of a nucleic acid sequence of Table I and/or Table II, or a nucleic acid sequence complementary to a nucleic acid sequence of Table I and/or Table II under conditions that allow less than or equal to 30% base pair mismatch.

Another embodiment of the present invention is an isolated nucleic acid molecule having a nucleic acid sequence that is at least 70% identical to a nucleic acid sequence of Table I and/or Table II or complements thereof as well as fragments of such sequences.

The present invention also relates to recombinant molecules, recombinant viruses and recombinant cells that include a nucleic acid molecule of the present invention. Also included are methods to produce such nucleic acid molecules, recombinant molecules, recombinant viruses and recombinant cells.

Another embodiment of the present invention includes an isolated flea HMT and/or HNC protein that is at least 70% identical to an amino acid sequence encoded by a nucleic acid sequence of Table I and/or Table U, and fragments thereof wherein such fragments can elicit an immune response against respective flea proteins or have activity comparable to respective flea proteins.

Another embodiment of the present invention includes an isolated protein encoded by a nucleic acid molecule that hybridizes with the complement of a nucleic acid sequence of Table I and/or Table II, under conditions that allow less than or equal to 30% base pair mismatch.

DETAILED DESCRIPTION OF THE INVENTION

The present invention provides for nucleic acid molecules isolated from the head and/or nerve cord of a flea, nucleic acid molecules isolated from the hindgut and/or Malpighian tubule of a flea, proteins encoded by such nucleic acid molecules, antibodies raised against such proteins, and inhibitors of such proteins. As used herein, nucleic acid molecules isolated from the head and/or nerve cord of a flea and proteins encoded by such nucleic acid molecules are also referred to as flea HNC, or HNC, nucleic acid molecules and proteins respectively; and nucleic molecules isolated from the hindgut and/or Malpighian tubules of a flea and proteins encoded by such nucleic acid molecules are referred to as flea HMT or HMT, nucleic acid molecules and proteins respectively. HNC nucleic acid molecules and HMT nucleic acid molecules of the present invention are nucleic acid molecules that are primarily expressed in flea HNC tissues and HMT tissues respectively, but which may be expressed in cells derived from flea tissues other than HNC and HMT. HNC and HMT nucleic acid molecules and proteins of the present invention can be isolated from a flea or prepared recombinantly or synthetically. IMT and HNC nucleic acid molecules of the present invention can be RNA or DNA; examples of nucleic acid molecules include, but are not limited to, complementary DNA (cDNA) molecules, genomic DNA molecules, synthetic DNA molecules, DNA molecules which are specific tags for messenger RNA derived from HMT and HNC tissues, and corresponding mRNA molecules. As such, a flea nucleic acid molecule of the present invention is not intended refer to an entire chromosome within which such a nucleic acid molecule is contained, however, a flea HMT or HNC cDNA of the present invention may include all regions such as regulatory regions that control production of flea peritrophin proteins encoded by such a cDNA (such as, but not limited to, transcription, translation or post-translation control regions) as well as the coding region itself, and any introns or non-translated coding regions. As used herein, the phrases "HMT and/or HNC protein" and "HMT and HNC protein" refer to a protein expressed by a flea HMT tissue, by a flea HNC tissue, or by both flea HMT and HNC tissues. As used herein, the phrases "HMT and/or HNC nucleic acid molecule" and "HMT and HNC nucleic acid molecule" refer to a nucleic acid molecule that can be isolated from a HMT cDNA library, from a HNC cDNA library, or from both libraries, or a gene corresponding thereto.

The present invention also provides for HMT and ENC DNA molecules that are specific tags for messenger RNA molecules derived from HMT and HNC tissues. Such DNA molecules can correspond to an entire or partial sequence of a messenger RNA, and therefore, a DNA molecule corresponding to such a messenger RNA molecule (i.e. a cDNA molecule), can encode a full-length or partial-length protein. A nucleic acid molecule encoding a partial-length protein can be used directly as a probe or indirectly to generate primers to identify and/or isolate a cDNA nucleic acid molecule encoding a corresponding, or structurally related, full-length protein. Such a partial cDNA nucleic acid molecule can also be used in a similar manner to identify a genomic nucleic acid molecule, such as a nucleic acid molecule that contains the complete gene including regulatory regions, exons and introns. Methods for using partial HMT and HNC cDNA molecules and sequences to isolate full-length transcripts and corresponding cDNA molecules are described in the examples herein below.

The proteins and nucleic acid molecules of the present invention can be obtained from their natural source, or can be produced using, for example, recombinant nucleic acid technology or chemical synthesis. Also included in the present invention is the use of these proteins and nucleic acid molecules as well as antibodies and inhibitory compounds thereto as therapeutic compositions to protect animals from flea infestation as well as in other applications, such as those disclosed below.

Flea HMT and HNC proteins and nucleic acid molecules of the present invention have utility because they represent novel targets for anti-arthropod vaccines and chemotherapeutic drugs. The products and processes of the present invention are advantageous because they enable the inhibition of arthropod development, metamorphosis, feeding, digestion and/or reproduction processes that involve HMT and/or ANC proteins.

The head and nerve cord of the flea, including antennae, brain, corpora cardiacum, corpora allata, and subesophageal and abdominal ganglion tissues are of interest as such tissues are highly enriched for transcripts that encode neuronal and endocrine targets, as well as targets involved in chemosensory and mechanosensory reception. By sequencing cDNA fragments from a library enriched in flea head and nerve cord nucleic acid sequences (referred to herein as HNC nucleic acid sequences), genes, and their respective full-length coding regions, integrally involved with flea neuronal and endocrine function are identified. Once identified, these genes can be further characterized and specific interference strategies are designed. As such, flea HNC proteins and nucleic acid molecules of the present invention have utility because they represent novel targets for anti-arthropod vaccines and chemotherapeutic drugs.

Blood-feeding insects such as fleas ingest large quantities of blood relative to their body weight and, as such, are adapted to reduce the volume of the ingested blood meal through the rapid elimination of water. In addition, the concentrations of sodium, potassium, and chloride ions in the blood meal are greater than in the hemolymph of fleas, necessitating the excretion of excessive amounts of these ions. The active transport of these ions from the hemolymph into the lumens of the Malpighian tubules and the hindgut drives the passive transport of water and other hemolymph contents into these organs as well. While passing through these organs, waste products from the hemolymph are excreted and needed nutrients, water, and salts are reabsorbed. As such, interfering with these essential processes is an important strategy for developing a product for controlling flea populations. By sequencing cDNA fragments from a library enriched in hindgut and Malpighian tubule nucleic acid sequences (referred to herein as HMT nucleic acid sequences), genes integrally involved with these processes, and their respective full-length coding regions, are identified. Once identified, these genes are further characterized and specific interference strategies can be designed. As such, flea HMT proteins and nucleic acid molecules of the present invention have utility because they represent novel targets for anti-arthropod vaccines and chemotherapeutic drugs.

One embodiment of the present invention is an isolated protein that includes a flea HMT and/or HNC protein. It is to be noted that the term "a" or "an" entity refers to one or more of that entity; for example, a protein, a nucleic acid molecule, an antibody and a therapeutic composition refers to "one or more" or "at least one" protein, nucleic acid molecule, antibody and therapeutic composition respectively. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, isolated flea IMT and/or HNC proteins of the present invention can be full-length proteins or any homologue of such proteins. An isolated protein of the present invention, including a homologue, can be identified in a straight-forward manner by the protein's ability to elicit an immune response against a flea HMT and/or HNC protein or by the protein's HMT and/or HNC activity. Examples of flea HMT and HNC homologue proteins include flea HMT and HNC proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue includes at least one epitope capable of eliciting an immune response against a flea HMT or HNC protein, and/or of binding to an antibody directed against a flea HMT or HNC protein. That is, when the homologue is administered to an animal as an immunogen, using techniques known to those skilled in the art, the animal will produce an immune response against at least one epitope of a natural flea HMT or HNC protein. The ability of a protein to effect an immune response can be measured using techniques known to those skilled in the art. As used herein, the term "epitope" refers to the smallest portion of a protein or other antigen capable of selectively binding to the anti-en binding site of an antibody or a T cell receptor. It is well accepted by those skilled in the art that the minimal size of a protein epitope is about four to six amino acids. As is appreciated by those skilled in the art, an epitope can include amino acids that naturally are contiguous to each other as well as amino acids that, due to the tertiary structure of the natural protein, are in sufficiently close proximity to form an epitope. According to the present invention, an epitope includes a portion of a protein comprising at least 4 amino acids, at least 5 amino acids, at least 6 amino acids, at least 10 amino acids, at least 15 amino acids, at least 20 amino acids, at least 25 amino acids, at least 30 amino acids, at least 35 amino acids, at least 40 amino acids or at least 50 amino acids in length.

In one embodiment of the present invention a flea homologue protein has HMT or HNC activity, i.e. the homologue exhibits an activity similar to its natural counterpart. Methods to detect and measure such activities are known to those skilled in the art.

Flea HMT and/or HNC homologue proteins can be the result of natural allelic variation or natural mutation. Flea HMT and/or HNC protein homologues of the present invention can also be produced using techniques known in the art including, but not limited to, direct modifications to the protein or modifications to the gene encoding the protein using, for example, classic or recombinant DNA techniques to effect random or targeted mutagenesis.

Flea HMT and HNC proteins of the present invention are encoded by flea HMT and HNC nucleic acid molecules, respectively. As used herein, flea HMT and HNC nucleic acid molecules include nucleic acid sequences related to natural flea HMT and HNC genes, and, preferably, to *Ctenocephalides felis* HMT and ENC genes. As used herein, flea HMT and HNC genes include all regions such as regulatory regions that control production of flea HMT and HNC proteins encoded by such genes (such as, but not limited to, transcription, translation or post-translation control regions) as well as the coding region itself, and any introns or non-translated coding regions. As used herein, a nucleic acid molecule that "includes" or "comprises" a sequence may include that sequence in one contiguous array, or may include the sequence as fragmented exons such as its often found for a flea gene. As used herein, the term "coding region" refers to a continuous linear array of nucleotides that translates into a protein. A full-length coding region is that coding region that is translated into a full-length, i.e., a complete protein as would be initially translated in its natural millieu, prior to any post-translational modifications.

TABLE I represents a variety of flea HNC nucleic acid molecules of the present invention.

| SEQ ID NO | Name |
|---|---|
| 1 | 2227-82HNC |
| 2 | 2228-51HNC |
| 3 | 2229-06HNC |
| 4 | 2229-42HNC |
| 5 | 2245-07HNC |
| 6 | 2245-93HNC |
| 7 | 2247-04HNC |
| 8 | 2229-44HNC |
| 9 | 2249-09HNC |
| 10 | 2249-10HNC |
| 11 | 2251-09HNC |
| 12 | 2215-13HNC |
| 13 | 2218-39HNC |
| 14 | 2218-82HNC |

TABLE II represents a variety of flea HMT nucleic acid molecules of the present invention.

| SEQ ID NO: | Name |
|---|---|
| 15 | 2084-03HMT |
| 16 | 2084-27HMT |
| 17 | 2084-41HMT |
| 18 | 2084-45HMT |
| 19 | 2084-47HMT |
| 20 | 2084-49HMT |
| 21 | 2084-51HMT |
| 22 | 2085-10HMT |
| 23 | 2085-23HMT |
| 24 | 2085-25HMT |
| 25 | 2085-41HMT |
| 26 | 2085-57HMT |
| 27 | 2086-22HMT |
| 28 | 2087-18HMT |
| 29 | 2088-24HMT |
| 30 | 2088-27HMT |
| 31 | 2088-30HMT |
| 32 | 2088-51HMT |
| 33 | 2088-53HMT |
| 34 | 2089-52HMT |
| 35 | 2091-32HMT |
| 36 | 2091-62HMT |
| 37 | 2092-34HMT |
| 38 | 2093-57HMT |
| 39 | 2094-14HMT |
| 40 | 2094-18HMT |
| 41 | 2094-46HMT |
| 42 | 2094-61HMT |
| 43 | 2095-14HMT |
| 44 | 2095-25HMT |
| 45 | 2095-50HMT |
| 46 | 2102-06HMT |
| 47 | 2102-25HMT |
| 48 | 2102-26HMT |
| 49 | 2103-15HMT |
| 50 | 2104-14HMT |
| 51 | 2104-16HMT |
| 52 | 2105-04HMT |
| 53 | 2105-07HMT |
| 54 | 2105-25HMT |
| 55 | 2105-41HMT |
| 56 | 2106-10HMT |
| 57 | 2107-21HMT |
| 58 | 2107-36HMT |
| 59 | 2108-08HMT |
| 60 | 2108-12HMT |
| 61 | 2108-22HMT |
| 62 | 2124-03HMT |
| 63 | 2154-17HMT |
| 64 | 2154-18HMT |

TABLE II-continued represents a variety of flea HMT nucleic acid molecules of the present invention.

| SEQ ID NO: | Name |
|---|---|
| 65 | 2154-49HMT |
| 66 | 2154-52HMT |
| 67 | 2154-55HMT |
| 68 | 2154-57HMT |
| 69 | 2156-05HMT |
| 70 | 2156-57HMT |
| 71 | 2157-40HMT |
| 72 | 2158-08HMT |
| 73 | 2158-20HMT |
| 74 | 2158-78HMT |
| 75 | 2159-78HMT |
| 76 | 2160-38HMT |
| 77 | 2160-87HMT |
| 78 | 2162-16HMT |
| 79 | 2162-20HMT |
| 80 | 2162-74HMT |
| 81 | 2166-25HMT |
| 82 | 2167-46HMT |
| 83 | 2169-34HMT |
| 84 | 2171-31HMT |
| 85 | 2171-81HMT |
| 86 | 2173-28HMT |
| 87 | 2173-61HMT |
| 88 | 2175-12HMT |
| 89 | 2175-26HMT |
| 90 | 2175-77HMT |
| 91 | 2177-26HMT |
| 92 | 2177-42HMT |
| 93 | 2177-50HMT |
| 94 | 2177-82HMT |
| 95 | 2181-65HMT |
| 96 | 2181-85HMT |
| 97 | 2183-34HMT |
| 98 | 2183-77HMT |
| 99 | 2183-90HMT |
| 100 | 2187-45HMT |
| 101 | 2188-28HMT |
| 102 | 2188-75HMT |
| 103 | 2191-26HMT |
| 104 | 2191-66HMT |
| 105 | 2192-23HMT |
| 106 | 2192-42HMT |
| 107 | 2193-50HMT |
| 108 | 2194-30HMT |
| 109 | 2194-37HMT |
| 110 | 2195-34HMT |
| 111 | 2195-80HMT |
| 112 | 2196-04HMT |
| 113 | 2196-29HMT |
| 114 | 2197-24HMT |
| 115 | 2202-47HMT |
| 116 | 2205-78HMT |
| 117 | 2253-02HMT |
| 118 | 2253-05HMT |
| 119 | 2253-07HMT |
| 120 | 2253-21HMT |
| 121 | 2253-73HMT |
| 122 | 2253-82HMT |
| 123 | 2253-83HMT |
| 124 | 2253-84HMT |
| 125 | 2253-96HMT |
| 126 | 2254-23HMT |
| 127 | 2254-24HMT |
| 128 | 2254-29HMT |
| 129 | 2254-40HMT |
| 130 | 2254-53HMT |
| 131 | 2254-57HMT |
| 132 | 2254-71HMT |
| 133 | 2254-85HMT |
| 134 | 2254-87HMT |
| 135 | 2254-92HMT |
| 136 | 2255-14HMT |
| 137 | 2255-15HMT |
| 138 | 2255-20HMT |
| 139 | 2255-21HMT |
| 140 | 2255-34HMT |
| 141 | 2255-52HMT |
| 142 | 2255-61HMT |
| 143 | 2255-72HMT |
| 144 | 2255-80HMT |
| 145 | 2256-05HMT |
| 146 | 2085-58HMT |
| 147 | 2086-20HMT |
| 148 | 2086-53HMT |
| 149 | 2087-06HMT |
| 150 | 2088-05HMT |
| 151 | 2088-17HMT |
| 152 | 2089-10HMT |
| 153 | 2092-40HMT |
| 154 | 2094-33HMT |
| 155 | 2094-47HMT |
| 156 | 2103-28HMT |
| 157 | 2103-58HMT |
| 158 | 2104-23HMT |
| 159 | 2104-59HMT |
| 160 | 2105-09HMT |
| 161 | 2106-14HMT |
| 162 | 2156-03HMT |
| 163 | 2156-14HMT |
| 164 | 2161-46HMT |
| 165 | 2162-93HMT |
| 166 | 2175-18HMT |
| 167 | 2185-19HMT |
| 168 | 2191-92HMT |
| 169 | 2195-06HMT |
| 170 | 2196-61HMT |
| 171 | 2253-13HMT |
| 172 | 2253-16HMT |
| 173 | 2253-19HMT |
| 174 | 2253-27HMT |
| 175 | 2253-40HMT |
| 176 | 2253-56HMT |
| 177 | 2253-68HMT |
| 178 | 2253-78HMT |
| 179 | 2253-87HMT |
| 180 | 2253-92HMT |
| 181 | 2254-43HMT |
| 182 | 2254-45HMT |
| 183 | 2254-51HMT |
| 184 | 2254-54HMT |
| 185 | 2254-66HMT |
| 186 | 2254-88HMT |
| 187 | 2254-96HMT |
| 188 | 2255-17HMT |
| 189 | 2255-19HMT |
| 190 | 2255-23HMT |
| 191 | 2255-25HMT |
| 192 | 2255-32HMT |
| 193 | 2255-39HMT |
| 194 | 2255-41HMT |
| 195 | 2255-45HMT |
| 196 | 2255-60HMT |
| 197 | 2255-62HMT |
| 198 | 2255-67HMT |
| 199 | 2255-77HMT |
| 200 | 2255-79HMT |
| 201 | 2255-82HMT |
| 202 | 2256-12HMT |
| 203 | 2256-22HMT |
| 204 | 2256-46HMT |
| 205 | 2256-54HMT |
| 206 | 2256-58HMT |
| 207 | 2256-64HMT |
| 208 | 2229-13HMT |
| 209 | 2229-17HMT |
| 210 | 2229-20HMT |
| 211 | 2229-31HMT |
| 212 | 2229-33HMT |
| 213 | 2229-34HMT |
| 214 | 2232-63HMT |

TABLE II-continued represents a variety of flea HMT nucleic acid molecules of the present invention.

| SEQ ID NO: | Name |
| --- | --- |
| 215 | 2232-70HMT |
| 216 | 2232-81HMT |
| 217 | 2232-96HMT |
| 218 | 2233-03HMT |
| 219 | 2233-04HMT |
| 220 | 2233-09HMT |
| 221 | 2233-14HMT |
| 222 | 2233-20HMT |
| 223 | 2233-33HMT |
| 224 | 2233-38HMT |
| 225 | 2233-39HMT |
| 226 | 2233-45HMT |
| 227 | 2233-54HMT |
| 228 | 2233-56HMT |
| 229 | 2233-60HMT |
| 230 | 2233-64HMT |
| 231 | 2233-70HMT |
| 232 | 2233-71HMT |
| 233 | 2233-75HMT |
| 234 | 2233-76HMT |
| 235 | 2233-77HMT |
| 236 | 2233-92HMT |
| 237 | 2233-95HMT |
| 238 | 2234-08HMT |
| 239 | 2234-15HMT |
| 240 | 2234-17HMT |
| 241 | 2234-18HMT |
| 242 | 2234-30HMT |
| 243 | 2234-33HMT |
| 244 | 2234-35HMT |
| 245 | 2234-37HMT |
| 246 | 2234-57HMT |
| 247 | 2234-65HMT |
| 248 | 2240-04HMT |
| 249 | 2241-07HMT |
| 250 | 2241-08HMT |
| 251 | 2241-09HMT |
| 252 | 2229-71HMT |
| 253 | 2229-86HMT |
| 254 | 2230-04HMT |
| 255 | 2230-09HMT |
| 256 | 2230-12HMT |
| 257 | 2230-13HMT |
| 258 | 2230-30HMT |
| 259 | 2230-31HMT |
| 260 | 2230-36HMT |
| 261 | 2230-40HMT |
| 262 | 2230-42HMT |
| 263 | 2230-44HMT |
| 264 | 2230-45HMT |
| 265 | 2230-61HMT |
| 266 | 2230-63HMT |
| 267 | 2230-68HMT |
| 268 | 2230-70HMT |
| 269 | 2230-72HMT |
| 270 | 2230-76HMT |
| 271 | 2230-78HMT |
| 272 | 2230-86HMT |
| 273 | 2230-92HMT |
| 274 | 2231-05HMT |
| 275 | 2231-06HMT |
| 276 | 2231-09HMT |
| 277 | 2231-12HMT |
| 278 | 2231-17HMT |
| 279 | 2231-30HMT |
| 280 | 2231-34HMT |
| 281 | 2231-45HMT |
| 282 | 2231-96HMT |
| 283 | 2232-07HMT |
| 284 | 2232-09HMT |
| 285 | 2232-13HMT |
| 286 | 2232-23HMT |
| 287 | 2232-31HMT |
| 288 | 2232-35HMT |
| 289 | 2232-40HMT |
| 290 | 2232-46HMT |
| 291 | 2232-54HMT |
| 292 | 2229-51HMT |
| 293 | 2230-60HMT |
| 294 | 2230-81HMT |
| 295 | 2231-03HMT |
| 296 | 2231-24HMT |
| 297 | 2231-56HMT |
| 298 | 2233-59HMT |
| 299 | 2234-12HMT |
| 300 | 2234-76HMT |
| 301 | 2234-86HMT |
| 302 | 2240-11HMT |
| 303 | 2240-14HMT |
| 304 | 2240-17HMT |
| 305 | 2240-23HMT |
| 306 | 2240-26HMT |
| 307 | 2240-28HMT |
| 308 | 2240-31HMT |
| 309 | 2240-44HMT |
| 310 | 2240-63HMT |
| 311 | 2240-66HMT |
| 312 | 2240-70HMT |
| 313 | 2240-72HMT |
| 314 | 2240-94HMT |
| 315 | 2241-10HMT |
| 316 | 2241-12HMT |
| 317 | 2241-40HMT |
| 318 | 2241-54HMT |
| 319 | 2241-56HMT |
| 320 | 2241-60HMT |
| 321 | 2241-66HMT |
| 322 | 2241-74HMT |
| 323 | 2241-82HMT |
| 324 | 2241-83HMT |
| 325 | 2241-86HMT |
| 326 | 2241-87HMT |
| 327 | 2243-10HMT |
| 328 | 2243-18HMT |
| 329 | 2243-20HMT |
| 330 | 2243-22HMT |
| 331 | 2243-27HMT |
| 332 | 2243-28HMT |
| 333 | 2243-31HMT |
| 334 | 2243-32HMT |
| 335 | 2243-38HMT |
| 336 | 2243-41HMT |
| 337 | 2243-45HMT |
| 338 | 2243-48HMT |
| 339 | 2243-52HMT |
| 340 | 2243-73HMT |
| 341 | 2243-86HMT |
| 342 | 2243-87HMT |
| 343 | 2243-94HMT |
| 344 | 2244-12HMT |
| 345 | 2244-25HMT |
| 346 | 2244-29HMT |
| 347 | 2244-44HMT |
| 348 | 2244-54HMT |
| 349 | 2244-71HMT |
| 350 | 2244-75HMT |
| 351 | 2084-19 |
| 352 | 2084-25 |
| 353 | 2084-57 |
| 354 | 2084-58 |
| 355 | 2084-64 |
| 356 | 2085-06 |
| 357 | 2085-12 |
| 358 | 2085-27 |
| 359 | 2085-28 |
| 360 | 2086-08 |
| 361 | 2086-14 |
| 362 | 2086-16 |
| 363 | 2086-21 |
| 364 | 2086-23 |

TABLE II-continued represents a variety of flea HMT nucleic acid molecules of the present invention.

| SEQ ID NO: | Name |
|---|---|
| 365 | 2086-46 |
| 366 | 2086-51 |
| 367 | 2086-56 |
| 368 | 2086-57 |
| 369 | 2086-59 |
| 370 | 2086-62 |
| 371 | 2087-05 |
| 372 | 2087-16 |
| 373 | 2087-19 |
| 374 | 2087-24 |
| 375 | 2087-53 |
| 376 | 2087-55 |
| 377 | 2088-06 |
| 378 | 2088-08 |
| 379 | 2088-12 |
| 380 | 2088-13 |
| 381 | 2088-14 |
| 382 | 2088-16 |
| 383 | 2088-18 |
| 384 | 2088-23 |
| 385 | 2088-28 |
| 386 | 2088-34 |
| 387 | 2088-42 |
| 388 | 2088-44 |
| 389 | 2088-45 |
| 390 | 2088-50 |
| 391 | 2089-04 |
| 392 | 2089-15 |
| 393 | 2089-16 |
| 394 | 2089-17 |
| 395 | 2089-18 |
| 396 | 2089-19 |
| 397 | 2089-24 |
| 398 | 2089-31 |
| 399 | 2089-38 |
| 400 | 2089-40 |
| 401 | 2089-41 |
| 402 | 2089-53 |
| 403 | 2089-58 |
| 404 | 2090-02 |
| 405 | 2090-12 |
| 406 | 2090-16 |
| 407 | 2090-29 |
| 408 | 2090-37 |
| 409 | 2090-39 |
| 410 | 2090-41 |
| 411 | 2090-50 |
| 412 | 2090-52 |
| 413 | 2090-56 |
| 414 | 2091-09 |
| 415 | 2091-15 |
| 416 | 2091-16 |
| 417 | 2091-18 |
| 418 | 2091-24 |
| 419 | 2091-25 |
| 420 | 2091-28 |
| 421 | 2091-52 |
| 422 | 2092-02 |
| 423 | 209206- |
| 424 | 2092-08 |
| 425 | 2092-15 |
| 426 | 2092-22 |
| 427 | 2092-24 |
| 428 | 2092-26 |
| 429 | 2092-30 |
| 430 | 2092-35 |
| 431 | 2092-53 |
| 432 | 2092-55 |
| 433 | 2092-63 |
| 434 | 2093-11 |
| 435 | 2093-19 |
| 436 | 2093-24 |
| 437 | 2093-27 |
| 438 | 2093-28 |
| 439 | 2093-33 |
| 440 | 2093-36 |
| 441 | 2093-37 |
| 442 | 2093-38 |
| 443 | 2093-40 |
| 444 | 2093-51 |
| 445 | 2093-52 |
| 446 | 2093-53 |
| 447 | 2093-55 |
| 448 | 2093-56 |
| 449 | 2093-60 |
| 450 | 2094-02 |
| 451 | 2094-04 |
| 452 | 2094-06 |
| 453 | 2094-09 |
| 454 | 2094-10 |
| 455 | 2094-13 |
| 456 | 2094-15 |
| 457 | 2094-23 |
| 458 | 2094-27 |
| 459 | 2094-29 |
| 460 | 2094-34 |
| 461 | 2094-37 |
| 462 | 2094-39 |
| 463 | 2094-41 |
| 464 | 2094-45 |
| 465 | 2094-49 |
| 466 | 2094-51 |
| 467 | 2094-53 |
| 468 | 2094-54 |
| 469 | 2094-59 |
| 470 | 2095-02 |
| 471 | 2095-07 |
| 472 | 2095-16 |
| 473 | 2095-19 |
| 474 | 2095-21 |
| 475 | 2095-24 |
| 476 | 2095-32 |
| 477 | 2095-35 |
| 478 | 2095-37 |
| 479 | 2095-39 |
| 480 | 2095-42 |
| 481 | 2095-44 |
| 482 | 2095-46 |
| 483 | 2095-49 |
| 484 | 2095-53 |
| 485 | 2095-56 |
| 486 | 2095-58 |
| 487 | 2095-61 |
| 488 | 2095-62 |
| 489 | 2095-64 |
| 490 | 2102-03 |
| 491 | 2102-04 |
| 492 | 2102-05 |
| 493 | 2102-07 |
| 494 | 2102-08 |
| 495 | 2102-10 |
| 496 | 2102-14 |
| 497 | 2102-15 |
| 498 | 2102-31 |
| 499 | 2102-34 |
| 500 | 2102-39 |
| 501 | 2102-40 |
| 502 | 2102-42 |
| 503 | 2102-43 |
| 504 | 2102-52 |
| 505 | 2102-56 |
| 506 | 2102-57 |
| 507 | 2102-62 |
| 508 | 2103-04 |
| 509 | 2103-06 |
| 510 | 2103-07 |
| 511 | 2103-10 |
| 512 | 2103-16 |
| 513 | 2103-18 |
| 514 | 2103-19 |

TABLE II-continued represents a variety of flea HMT nucleic acid molecules of the present invention.

| SEQ ID NO: | Name |
|---|---|
| 515 | 2103-20 |
| 516 | 2103-21 |
| 517 | 2103-22 |
| 518 | 2103-23 |
| 519 | 2103-25 |
| 520 | 2103-26 |
| 521 | 2103-32 |
| 522 | 2103-34 |
| 523 | 2103-36 |
| 524 | 2103-38 |
| 525 | 2103-39 |
| 526 | 2103-42 |
| 527 | 2103-43 |
| 528 | 2103-46 |
| 529 | 2103-51 |
| 530 | 2103-52 |
| 531 | 2103-54 |
| 532 | 2103-59 |
| 533 | 2103-64 |
| 534 | 2104-02 |
| 535 | 2104-09 |
| 536 | 2104-11 |
| 537 | 2104-12 |
| 538 | 2104-17 |
| 539 | 2104-19 |
| 540 | 2104-27 |
| 541 | 2104-30 |
| 542 | 2104-33 |
| 543 | 2104-36 |
| 544 | 2104-37 |
| 545 | 2104-39 |
| 546 | 2104-42 |
| 547 | 2104-49 |
| 548 | 2104-52 |
| 549 | 2104-53 |
| 550 | 2104-57 |
| 551 | 2104-62 |
| 552 | 2105-03 |
| 553 | 2105-05 |
| 554 | 2105-06 |
| 555 | 2105-08 |
| 556 | 2105-13 |
| 557 | 2105-22 |
| 558 | 2105-24 |
| 559 | 2105-26 |
| 560 | 2105-27 |
| 561 | 2105-29 |
| 562 | 2105-30 |
| 563 | 2105-36 |
| 564 | 2105-39 |
| 565 | 2105-47 |
| 566 | 2105-49 |
| 567 | 2105-52 |
| 568 | 2105-58 |
| 569 | 2105-59 |
| 570 | 2105-60 |
| 571 | 2106-03 |
| 572 | 2106-05 |
| 573 | 2106-06 |
| 574 | 2106-08 |
| 575 | 2106-13 |
| 576 | 2106-22 |
| 577 | 2106-24 |
| 578 | 2106-26 |
| 579 | 2106-27 |
| 580 | 2106-29 |
| 581 | 2106-30 |
| 582 | 2106-36 |
| 583 | 2106-39 |
| 584 | 2106-47 |
| 585 | 2106-49 |
| 586 | 2106-52 |
| 587 | 2106-58 |
| 588 | 2106-59 |
| 589 | 2106-60 |
| 590 | 2107-05 |
| 591 | 2107-07 |
| 592 | 2107-08 |
| 593 | 2107-14 |
| 594 | 2107-20 |
| 595 | 2107-23 |
| 596 | 2107-27 |
| 597 | 2107-31 |
| 598 | 2107-33 |
| 599 | 2107-34 |
| 600 | 2107-35 |
| 601 | 2107-42 |
| 602 | 2107-44 |
| 603 | 2107-47 |
| 604 | 2107-48 |
| 605 | 2107-49 |
| 606 | 2107-51 |
| 607 | 2107-53 |
| 608 | 2107-56 |
| 609 | 2107-60 |
| 610 | 2107-62 |
| 611 | 2107-63 |
| 612 | 2108-15 |
| 613 | 2108-16 |
| 614 | 2108-18 |
| 615 | 2108-20 |
| 616 | 2108-24 |
| 617 | 2108-25 |
| 618 | 2108-30 |
| 619 | 2108-32 |
| 620 | 2108-33 |
| 621 | 2108-34 |
| 622 | 2108-43 |
| 623 | 2108-45 |
| 624 | 2108-50 |
| 625 | 2108-55 |
| 626 | 2108-61 |
| 627 | 2108-62 |
| 628 | 2109-03 |
| 629 | 2109-05 |
| 630 | 2109-09 |
| 631 | 2109-11 |
| 632 | 2109-12 |
| 633 | 2109-14 |
| 634 | 2109-15 |
| 635 | 2109-17 |
| 636 | 2109-20 |
| 637 | 2109-22 |
| 638 | 2109-23 |
| 639 | 2109-25 |
| 640 | 2109-27 |
| 641 | 2109-29 |
| 642 | 2109-32 |
| 643 | 2109-33 |
| 644 | 2109-34 |
| 645 | 2109-36 |
| 646 | 2109-41 |
| 647 | 2109-43 |
| 648 | 2109-45 |
| 649 | 2109-46 |
| 650 | 2109-48 |
| 651 | 2109-49 |
| 652 | 2109-50 |
| 653 | 2109-57 |
| 654 | 2109-60 |
| 655 | 2109-61 |
| 656 | 2109-62 |
| 657 | 2109-63 |
| 658 | 2154-02 |
| 659 | 2154-03 |
| 660 | 2154-05 |
| 661 | 2154-07 |
| 662 | 2154-12 |
| 663 | 2154-13 |
| 664 | 2154-14 |

TABLE II-continued represents a variety of flea HMT nucleic acid molecules of the present invention.

| SEQ ID NO: | Name |
|---|---|
| 665 | 2154-15 |
| 666 | 2154-19 |
| 667 | 2154-22 |
| 668 | 2154-26 |
| 669 | 2154-35 |
| 670 | 2154-37 |
| 671 | 2154-39 |
| 672 | 2154-40 |
| 673 | 2154-44 |
| 674 | 2154-53 |
| 675 | 2154-59 |
| 676 | 2154-62 |
| 677 | 2154-63 |
| 678 | 2154-67 |
| 679 | 2154-69 |
| 680 | 2154-88 |
| 681 | 2156-04 |
| 682 | 2156-08 |
| 683 | 2156-13 |
| 684 | 2156-16 |
| 685 | 2156-19 |
| 686 | 2156-20 |
| 687 | 2156-22 |
| 688 | 2156-24 |
| 689 | 2156-25 |
| 690 | 2156-30 |
| 691 | 2156-31 |
| 692 | 2156-32 |
| 693 | 2156-33 |
| 694 | 2156-35 |
| 695 | 2156-39 |
| 696 | 2156-45 |
| 697 | 2156-46 |
| 698 | 2156-49 |
| 699 | 2156-55 |
| 700 | 2156-61 |
| 701 | 2156-64 |
| 702 | 2157-03 |
| 703 | 2157-04 |
| 704 | 2157-07 |
| 705 | 2157-09 |
| 706 | 2157-13 |
| 707 | 2157-17 |
| 708 | 2157-18 |
| 709 | 2157-19 |
| 710 | 2157-22 |
| 711 | 2157-23 |
| 712 | 2157-24 |
| 713 | 2157-25 |
| 714 | 2157-26 |
| 715 | 2157-28 |
| 716 | 2157-35 |
| 717 | 2157-37 |
| 718 | 2157-38 |
| 719 | 2157-41 |
| 720 | 2157-42 |
| 721 | 2157-46 |
| 722 | 2157-49 |
| 723 | 2157-50 |
| 724 | 2157-52 |
| 725 | 2157-57 |
| 726 | 2157-63 |
| 727 | 2157-65 |
| 728 | 2157-71 |
| 729 | 2157-72 |
| 730 | 2157-74 |
| 731 | 2157-75 |
| 732 | 2157-80 |
| 733 | 2157-93 |
| 734 | 2158-08 |
| 735 | 2158-10 |
| 736 | 2158-13 |
| 737 | 2158-15 |
| 738 | 2158-16 |
| 739 | 2158-20 |
| 740 | 2158-26 |
| 741 | 2158-32 |
| 742 | 2158-38 |
| 743 | 2158-40 |
| 744 | 2158-43 |
| 745 | 2158-44 |
| 746 | 2158-45 |
| 747 | 2158-46 |
| 748 | 2159-16 |
| 749 | 2159-18 |
| 750 | 2159-24 |
| 751 | 2159-26 |
| 752 | 2159-28 |
| 753 | 2159-33 |
| 754 | 2159-37 |
| 755 | 2159-38 |
| 756 | 2159-40 |
| 757 | 2159-42 |
| 758 | 2159-43 |
| 759 | 2159-44 |
| 760 | 2159-45 |
| 761 | 2159-46 |
| 762 | 2159-50 |
| 763 | 2159-52 |
| 764 | 2159-61 |
| 765 | 2159-62 |
| 766 | 2159-65 |
| 767 | 2159-67 |
| 768 | 2159-70 |
| 769 | 2159-71 |
| 770 | 2159-72 |
| 771 | 2159-73 |
| 772 | 2159-74 |
| 773 | 2159-80 |
| 774 | 2159-83 |
| 775 | 2159-86 |
| 776 | 2159-89 |
| 777 | 2159-90 |
| 778 | 2159-93 |
| 779 | 2159-95 |
| 780 | 2160-04 |
| 781 | 2160-05 |
| 782 | 2160-08 |
| 783 | 2160-10 |
| 784 | 2160-15 |
| 785 | 2160-20 |
| 786 | 2160-22 |
| 787 | 2160-24 |
| 788 | 2160-33 |
| 789 | 2160-37 |
| 790 | 2160-40 |
| 791 | 2160-41 |
| 792 | 2160-43 |
| 793 | 2160-46 |
| 794 | 2160-51 |
| 795 | 2160-52 |
| 796 | 2160-56 |
| 797 | 2160-57 |
| 798 | 2160-64 |
| 799 | 2160-66 |
| 800 | 2160-72 |
| 801 | 2160-73 |
| 802 | 2160-76 |
| 803 | 2160-78 |
| 804 | 2160-92 |
| 805 | 2160-94 |
| 806 | 2160-95 |
| 807 | 2160-96 |
| 808 | 2161-02 |
| 809 | 2161-22 |
| 810 | 2161-24 |
| 811 | 2161-25 |
| 812 | 2161-26 |
| 813 | 2161-27 |
| 814 | 2161-29 |

TABLE II-continued represents a variety of flea HMT nucleic acid molecules of the present invention.

| SEQ ID NO: | Name |
|---|---|
| 815 | 2161-30 |
| 816 | 2161-31 |
| 817 | 2161-32 |
| 818 | 2161-33 |
| 819 | 2161-36 |
| 820 | 2161-41 |
| 821 | 2161-42 |
| 822 | 2161-50 |
| 823 | 2161-51 |
| 824 | 2161-53 |
| 825 | 2161-55 |
| 826 | 2161-61 |
| 827 | 2161-63 |
| 828 | 2161-66 |
| 829 | 2161-68 |
| 830 | 2161-71 |
| 831 | 2161-73 |
| 832 | 2161-84 |
| 833 | 2162-04 |
| 834 | 2162-07 |
| 835 | 2162-09 |
| 836 | 2162-10 |
| 837 | 2162-14 |
| 838 | 2162-15 |
| 839 | 2162-17 |
| 840 | 2162-19 |
| 841 | 2162-22 |
| 842 | 2162-23 |
| 843 | 2162-27 |
| 844 | 2162-29 |
| 845 | 2162-37 |
| 846 | 2162-39 |
| 847 | 2162-43 |
| 848 | 2162-51 |
| 849 | 2162-52 |
| 850 | 2162-54 |
| 851 | 2162-55 |
| 852 | 2162-56 |
| 853 | 2162-57 |
| 854 | 2162-58 |
| 855 | 2162-60 |
| 856 | 2162-61 |
| 857 | 2162-65 |
| 858 | 2162-67 |
| 859 | 2162-70 |
| 860 | 2162-76 |
| 861 | 2162-77 |
| 862 | 2162-79 |
| 863 | 2162-82 |
| 864 | 2162-84 |
| 865 | 2162-85 |
| 866 | 2162-86 |
| 867 | 2162-89 |
| 868 | 2162-90 |
| 869 | 2162-94 |
| 870 | 2163-05 |
| 871 | 2163-06 |
| 872 | 2163-08 |
| 873 | 2163-09 |
| 874 | 2163-10 |
| 875 | 2163-12 |
| 876 | 2163-13 |
| 877 | 2163-14 |
| 878 | 2163-15 |
| 879 | 2163-16 |
| 880 | 2163-17 |
| 881 | 2163-19 |
| 882 | 2163-20 |
| 883 | 2163-30 |
| 884 | 2163-33 |
| 885 | 2163-34 |
| 886 | 2163-35 |
| 887 | 2163-37 |
| 888 | 2163-38 |
| 889 | 2163-39 |
| 890 | 2163-40 |
| 891 | 2163-41 |
| 892 | 2163-46 |
| 893 | 2163-47 |
| 894 | 2163-59 |
| 895 | 2163-63 |
| 896 | 2163-66 |
| 897 | 2163-67 |
| 898 | 2163-68 |
| 899 | 2163-69 |
| 900 | 2163-70 |
| 901 | 2163-72 |
| 902 | 2163-74 |
| 903 | 2163-75 |
| 904 | 2163-80 |
| 905 | 2163-88 |
| 906 | 2163-96 |
| 907 | 2164-02 |
| 908 | 2164-03 |
| 909 | 2164-04 |
| 910 | 2164-05 |
| 911 | 2164-06 |
| 912 | 2164-09 |
| 913 | 2164-10 |
| 914 | 2164-11 |
| 915 | 2164-12 |
| 916 | 2164-14 |
| 917 | 2164-15 |
| 918 | 2164-17 |
| 919 | 2164-20 |
| 920 | 2164-21 |
| 921 | 2164-22 |
| 922 | 2164-23 |
| 923 | 2164-26 |
| 924 | 2164-27 |
| 925 | 2164-28 |
| 926 | 2164-29 |
| 927 | 2164-30 |
| 928 | 2164-31 |
| 929 | 2164-32 |
| 930 | 2164-33 |
| 931 | 2164-34 |
| 932 | 2164-36 |
| 933 | 2164-37 |
| 934 | 2164-41 |
| 935 | 2164-42 |
| 936 | 2164-44 |
| 937 | 2164-46 |
| 938 | 2164-48 |
| 939 | 2164-49 |
| 940 | 2164-50 |
| 941 | 2164-51 |
| 942 | 2164-52 |
| 943 | 2164-53 |
| 944 | 2164-54 |
| 945 | 2164-56 |
| 946 | 2164-57 |
| 947 | 2164-58 |
| 948 | 2164-59 |
| 949 | 2164-61 |
| 950 | 2164-62 |
| 951 | 2164-68 |
| 952 | 2164-69 |
| 953 | 2164-70 |
| 954 | 2164-71 |
| 955 | 2164-72 |
| 956 | 2164-73 |
| 957 | 2164-74 |
| 958 | 2164-75 |
| 959 | 2164-77 |
| 960 | 2164-78 |
| 961 | 2164-79 |
| 962 | 2164-80 |
| 963 | 2164-81 |
| 964 | 2164-83 |

TABLE II-continued represents a variety of flea HMT nucleic acid molecules of the present invention.

| SEQ ID NO: | Name |
|---|---|
| 965 | 2164-84 |
| 966 | 2164-85 |
| 967 | 2164-86 |
| 968 | 2164-87 |
| 969 | 2164-88 |
| 970 | 2164-89 |
| 971 | 2164-91 |
| 972 | 2164-92 |
| 973 | 2164-93 |
| 974 | 2164-94 |
| 975 | 2164-95 |
| 976 | 2164-96 |
| 977 | 2165-02 |
| 978 | 2165-03 |
| 979 | 2165-07 |
| 980 | 2165-09 |
| 981 | 2165-10 |
| 982 | 2165-11 |
| 983 | 2165-13 |
| 984 | 2165-15 |
| 985 | 2165-19 |
| 986 | 2165-22 |
| 987 | 2165-23 |
| 988 | 2165-25 |
| 989 | 2165-29 |
| 990 | 2165-34 |
| 991 | 2165-38 |
| 992 | 2165-39 |
| 993 | 2165-40 |
| 994 | 2165-43 |
| 995 | 2165-44 |
| 996 | 2165-46 |
| 997 | 2165-49 |
| 998 | 2165-50 |
| 999 | 2165-51 |
| 1000 | 2165-52 |
| 1001 | 2165-53 |
| 1002 | 2165-55 |
| 1003 | 2165-61 |
| 1004 | 2165-62 |
| 1005 | 2165-71 |
| 1006 | 2165-72 |
| 1007 | 2165-73 |
| 1008 | 2165-75 |
| 1009 | 2165-77 |
| 1010 | 2165-78 |
| 1011 | 2165-79 |
| 1012 | 2165-80 |
| 1013 | 2165-81 |
| 1014 | 2165-91 |
| 1015 | 2165-92 |
| 1016 | 2165-93 |
| 1017 | 2165-95 |
| 1018 | 2165-96 |
| 1019 | 2166-04 |
| 1020 | 2166-06 |
| 1021 | 2166-07 |
| 1022 | 2166-08 |
| 1023 | 2166-13 |
| 1024 | 2166-14 |
| 1025 | 2166-16 |
| 1026 | 2166-18 |
| 1027 | 2166-20 |
| 1028 | 2166-30 |
| 1029 | 2166-34 |
| 1030 | 2166-36 |
| 1031 | 2166-37 |
| 1032 | 2166-38 |
| 1033 | 2166-39 |
| 1034 | 2166-43 |
| 1035 | 2166-45 |
| 1036 | 2166-48 |
| 1037 | 2166-49 |
| 1038 | 2166-52 |
| 1039 | 2166-54 |
| 1040 | 2166-55 |
| 1041 | 2166-57 |
| 1042 | 2166-59 |
| 1043 | 2166-63 |
| 1044 | 2166-66 |
| 1045 | 2166-67 |
| 1046 | 2166-68 |
| 1047 | 2166-69 |
| 1048 | 2166-70 |
| 1049 | 2166-72 |
| 1050 | 2166-74 |
| 1051 | 2166-85 |
| 1052 | 2166-86 |
| 1053 | 2167-02 |
| 1054 | 2167-06 |
| 1055 | 2167-08 |
| 1056 | 2167-11 |
| 1057 | 2167-12 |
| 1058 | 2167-17 |
| 1059 | 2167-19 |
| 1060 | 2167-21 |
| 1061 | 2167-22 |
| 1062 | 2167-23 |
| 1063 | 2167-24 |
| 1064 | 2167-27 |
| 1065 | 2167-29 |
| 1066 | 2167-30 |
| 1067 | 2167-32 |
| 1068 | 2167-34 |
| 1069 | 2167-37 |
| 1070 | 2167-38 |
| 1071 | 2167-39 |
| 1072 | 2167-41 |
| 1073 | 2167-43 |
| 1074 | 2167-50 |
| 1075 | 2167-54 |
| 1076 | 2167-55 |
| 1077 | 2167-57 |
| 1078 | 2167-58 |
| 1079 | 2167-64 |
| 1080 | 2167-65 |
| 1081 | 2167-71 |
| 1082 | 2167-72 |
| 1083 | 2167-73 |
| 1084 | 2167-74 |
| 1085 | 2167-75 |
| 1086 | 2167-76 |
| 1087 | 2167-77 |
| 1088 | 2167-81 |
| 1089 | 2167-83 |
| 1090 | 2167-86 |
| 1091 | 2167-89 |
| 1092 | 2167-93 |
| 1093 | 2167-94 |
| 1094 | 2167-95 |
| 1095 | 2169-02 |
| 1096 | 2169-03 |
| 1097 | 2169-11 |
| 1098 | 2169-15 |
| 1099 | 2169-18 |
| 1100 | 2169-20 |
| 1101 | 2169-21 |
| 1102 | 2169-23 |
| 1103 | 2169-25 |
| 1104 | 2169-28 |
| 1105 | 2169-29 |
| 1106 | 2169-31 |
| 1107 | 2169-36 |
| 1108 | 2169-37 |
| 1109 | 2169-38 |
| 1110 | 2169-45 |
| 1111 | 2169-48 |
| 1112 | 2169-50 |
| 1113 | 2169-53 |
| 1114 | 2169-54 |

TABLE II-continued represents a variety of flea HMT nucleic acid molecules of the present invention.

| SEQ ID NO: | Name |
|---|---|
| 1115 | 2169-55 |
| 1116 | 2169-56 |
| 1117 | 2169-58 |
| 1118 | 2169-59 |
| 1119 | 2169-60 |
| 1120 | 2169-61 |
| 1121 | 2169-62 |
| 1122 | 2169-63 |
| 1123 | 2169-64 |
| 1124 | 2169-67 |
| 1125 | 2169-68 |
| 1126 | 2169-72 |
| 1127 | 2169-73 |
| 1128 | 2169-75 |
| 1129 | 2169-76 |
| 1130 | 2169-77 |
| 1131 | 2169-83 |
| 1132 | 2169-84 |
| 1133 | 2169-87 |
| 1134 | 2169-89 |
| 1135 | 2169-90 |
| 1136 | 2169-92 |
| 1137 | 2169-93 |
| 1138 | 2169-94 |
| 1139 | 2171-02 |
| 1140 | 2171-05 |
| 1141 | 2171-07 |
| 1142 | 2171-08 |
| 1143 | 2171-10 |
| 1144 | 2171-12 |
| 1145 | 2171-14 |
| 1146 | 2171-15 |
| 1147 | 2171-18 |
| 1148 | 2171-19 |
| 1149 | 2171-25 |
| 1150 | 2171-26 |
| 1151 | 2171-27 |
| 1152 | 2171-28 |
| 1153 | 2171-29 |
| 1154 | 2171-36 |
| 1155 | 2171-38 |
| 1156 | 2171-42 |
| 1157 | 2171-44 |
| 1158 | 2171-45 |
| 1159 | 2171-48 |
| 1160 | 2171-49 |
| 1161 | 2171-53 |
| 1162 | 2171-58 |
| 1163 | 2171-59 |
| 1164 | 2171-62 |
| 1165 | 2171-65 |
| 1166 | 2171-67 |
| 1167 | 2171-70 |
| 1168 | 2171-71 |
| 1169 | 2171-74 |
| 1170 | 2171-75 |
| 1171 | 2171-77 |
| 1172 | 2171-78 |
| 1173 | 2171-83 |
| 1174 | 2171-86 |
| 1175 | 2171-87 |
| 1176 | 2171-90 |
| 1177 | 2171-91 |
| 1178 | 2171-94 |
| 1179 | 2171-95 |
| 1180 | 2171-96 |
| 1181 | 2173-03 |
| 1182 | 2173-04 |
| 1183 | 2173-05 |
| 1184 | 2173-06 |
| 1185 | 2173-15 |
| 1186 | 2173-17 |
| 1187 | 2173-20 |
| 1188 | 2173-24 |
| 1189 | 2173-26 |
| 1190 | 2173-27 |
| 1191 | 2173-30 |
| 1192 | 2173-31 |
| 1193 | 2173-33 |
| 1194 | 2173-35 |
| 1195 | 2173-37 |
| 1196 | 2173-41 |
| 1197 | 2173-46 |
| 1198 | 2173-49 |
| 1199 | 2173-60 |
| 1200 | 2173-62 |
| 1201 | 2173-65 |
| 1202 | 2173-66 |
| 1203 | 2173-69 |
| 1204 | 2173-72 |
| 1205 | 2173-73 |
| 1206 | 2173-77 |
| 1207 | 2173-79 |
| 1208 | 2173-80 |
| 1209 | 2173-82 |
| 1210 | 2173-87 |
| 1211 | 2173-88 |
| 1212 | 2173-89 |
| 1213 | 2173-92 |
| 1214 | 2175-03 |
| 1215 | 2175-05 |
| 1216 | 2175-09 |
| 1217 | 2175-10 |
| 1218 | 2175-11 |
| 1219 | 2175-14 |
| 1220 | 2175-16 |
| 1221 | 2175-17 |
| 1222 | 2175-21 |
| 1223 | 2175-22 |
| 1224 | 2175-23 |
| 1225 | 2175-27 |
| 1226 | 2175-29 |
| 1227 | 2175-30 |
| 1228 | 2175-31 |
| 1229 | 2175-33 |
| 1230 | 2175-35 |
| 1231 | 2175-36 |
| 1232 | 2175-40 |
| 1233 | 2175-41 |
| 1234 | 2175-42 |
| 1235 | 2175-43 |
| 1236 | 2175-47 |
| 1237 | 2175-50 |
| 1238 | 2175-51 |
| 1239 | 2175-52 |
| 1240 | 2175-53 |
| 1241 | 2175-54 |
| 1242 | 2175-55 |
| 1243 | 2175-56 |
| 1244 | 2175-57 |
| 1245 | 2175-59 |
| 1246 | 2175-60 |
| 1247 | 2175-61 |
| 1248 | 2175-63 |
| 1249 | 2175-65 |
| 1250 | 2175-66 |
| 1251 | 2175-67 |
| 1252 | 2175-68 |
| 1253 | 2175-69 |
| 1254 | 2175-70 |
| 1255 | 2175-79 |
| 1256 | 2175-80 |
| 1257 | 2175-81 |
| 1258 | 2175-85 |
| 1259 | 2175-87 |
| 1260 | 2175-93 |
| 1261 | 2175-94 |
| 1262 | 2175-95 |
| 1263 | 2177-02 |
| 1264 | 2177-03 |

TABLE II-continued represents a variety of flea HMT nucleic acid molecules of the present invention.

| SEQ ID NO: | Name |
|---|---|
| 1265 | 2177-04 |
| 1266 | 2177-05 |
| 1267 | 2177-09 |
| 1268 | 2177-25 |
| 1269 | 2177-28 |
| 1270 | 2177-30 |
| 1271 | 2177-32 |
| 1272 | 2177-35 |
| 1273 | 2177-36 |
| 1274 | 2177-37 |
| 1275 | 2177-38 |
| 1276 | 2177-43 |
| 1277 | 2177-49 |
| 1278 | 2177-55 |
| 1279 | 2177-56 |
| 1280 | 2177-58 |
| 1281 | 2177-62 |
| 1282 | 2177-63 |
| 1283 | 2177-65 |
| 1284 | 2177-66 |
| 1285 | 2177-67 |
| 1286 | 2177-68 |
| 1287 | 2177-71 |
| 1288 | 2177-73 |
| 1289 | 2177-75 |
| 1290 | 2177-76 |
| 1291 | 2177-77 |
| 1292 | 2177-83 |
| 1293 | 2177-84 |
| 1294 | 2177-85 |
| 1295 | 2177-87 |
| 1296 | 2177-88 |
| 1297 | 2177-89 |
| 1298 | 2177-90 |
| 1299 | 2177-93 |
| 1300 | 2177-95 |
| 1301 | 2179-04 |
| 1302 | 2179-06 |
| 1303 | 2179-08 |
| 1304 | 2179-13 |
| 1305 | 2179-14 |
| 1306 | 2179-15 |
| 1307 | 2179-16 |
| 1308 | 2179-17 |
| 1309 | 2179-21 |
| 1310 | 2179-25 |
| 1311 | 2179-26 |
| 1312 | 2179-31 |
| 1313 | 2179-33 |
| 1314 | 2179-34 |
| 1315 | 2179-36 |
| 1316 | 2179-37 |
| 1317 | 2179-38 |
| 1318 | 2179-40 |
| 1319 | 2179-41 |
| 1320 | 2179-45 |
| 1321 | 2179-50 |
| 1322 | 2179-55 |
| 1323 | 2179-57 |
| 1324 | 2179-58 |
| 1325 | 2179-60 |
| 1326 | 2179-61 |
| 1327 | 2179-64 |
| 1328 | 2179-65 |
| 1329 | 2179-66 |
| 1330 | 2179-67 |
| 1331 | 2179-68 |
| 1332 | 2179-70 |
| 1333 | 2179-71 |
| 1334 | 2179-72 |
| 1335 | 2179-74 |
| 1336 | 2179-75 |
| 1337 | 2179-76 |
| 1338 | 2179-78 |
| 1339 | 2179-80 |
| 1340 | 2179-81 |
| 1341 | 2179-82 |
| 1342 | 2179-84 |
| 1343 | 2179-85 |
| 1344 | 2179-89 |
| 1345 | 2179-90 |
| 1346 | 2179-91 |
| 1347 | 2179-92 |
| 1348 | 2179-93 |
| 1349 | 2179-95 |
| 1350 | 2179-96 |
| 1351 | 2181-03 |
| 1352 | 2181-06 |
| 1353 | 2181-07 |
| 1354 | 2181-08 |
| 1355 | 2181-11 |
| 1356 | 2181-13 |
| 1357 | 2181-15 |
| 1358 | 2181-16 |
| 1359 | 2181-17 |
| 1360 | 2181-20 |
| 1361 | 2181-21 |
| 1362 | 2181-25 |
| 1363 | 2181-28 |
| 1364 | 2181-30 |
| 1365 | 2181-31 |
| 1366 | 2181-32 |
| 1367 | 2181-33 |
| 1368 | 2181-34 |
| 1369 | 2181-38 |
| 1370 | 2181-40 |
| 1371 | 2181-41 |
| 1372 | 2181-43 |
| 1373 | 2181-44 |
| 1374 | 2181-47 |
| 1375 | 2181-48 |
| 1376 | 2181-49 |
| 1377 | 2181-53 |
| 1378 | 2181-54 |
| 1379 | 2181-55 |
| 1380 | 2181-57 |
| 1381 | 2181-58 |
| 1382 | 2181-59 |
| 1383 | 2181-60 |
| 1384 | 2181-61 |
| 1385 | 2181-62 |
| 1386 | 2181-63 |
| 1387 | 2181-67 |
| 1388 | 2181-70 |
| 1389 | 2181-71 |
| 1390 | 2181-72 |
| 1391 | 2181-74 |
| 1392 | 2181-77 |
| 1393 | 2181-78 |
| 1394 | 2181-79 |
| 1395 | 2181-80 |
| 1396 | 2181-83 |
| 1397 | 2181-85 |
| 1398 | 2181-86 |
| 1399 | 2181-88 |
| 1400 | 2181-89 |
| 1401 | 2181-90 |
| 1402 | 2181-95 |
| 1403 | 2181-96 |
| 1404 | 2183-02 |
| 1405 | 2183-03 |
| 1406 | 2183-04 |
| 1407 | 2183-09 |
| 1408 | 2183-12 |
| 1409 | 2183-18 |
| 1410 | 2183-19 |
| 1411 | 2183-23 |
| 1412 | 2183-26 |
| 1413 | 2183-27 |
| 1414 | 2183-29 |

TABLE II-continued represents a variety of flea HMT nucleic acid molecules of the present invention.

| SEQ ID NO: | Name |
|---|---|
| 1415 | 2183-31 |
| 1416 | 2183-34 |
| 1417 | 2183-35 |
| 1418 | 2183-37 |
| 1419 | 2183-42 |
| 1420 | 2183-43 |
| 1421 | 2183-47 |
| 1422 | 2183-48 |
| 1423 | 2183-54 |
| 1424 | 2183-56 |
| 1425 | 2183-57 |
| 1426 | 2183-60 |
| 1427 | 2183-63 |
| 1428 | 2183-64 |
| 1429 | 2183-66 |
| 1430 | 2183-67 |
| 1431 | 2183-72 |
| 1432 | 2183-73 |
| 1433 | 2183-74 |
| 1434 | 2183-75 |
| 1435 | 2183-76 |
| 1436 | 2183-78 |
| 1437 | 2183-79 |
| 1438 | 2183-80 |
| 1439 | 2183-82 |
| 1440 | 2183-83 |
| 1441 | 2183-84 |
| 1442 | 2183-87 |
| 1443 | 2183-89 |
| 1444 | 2183-91 |
| 1445 | 2183-92 |
| 1446 | 2183-94 |
| 1447 | 2185-02 |
| 1448 | 2185-03 |
| 1449 | 2185-06 |
| 1450 | 2185-07 |
| 1451 | 2185-08 |
| 1452 | 2185-11 |
| 1453 | 2185-13 |
| 1454 | 2185-14 |
| 1455 | 2185-17 |
| 1456 | 2185-18 |
| 1457 | 2185-25 |
| 1458 | 2185-26 |
| 1459 | 2185-30 |
| 1460 | 2185-31 |
| 1461 | 2185-32 |
| 1462 | 2185-35 |
| 1463 | 2185-37 |
| 1464 | 2185-39 |
| 1465 | 2185-40 |
| 1466 | 2185-42 |
| 1467 | 2185-45 |
| 1468 | 2185-46 |
| 1469 | 2185-47 |
| 1470 | 2185-50 |
| 1471 | 2185-58 |
| 1472 | 2185-63 |
| 1473 | 2185-64 |
| 1474 | 2185-65 |
| 1475 | 2185-67 |
| 1476 | 2185-68 |
| 1477 | 2185-72 |
| 1478 | 2185-73 |
| 1479 | 2185-74 |
| 1480 | 2185-76 |
| 1481 | 2185-77 |
| 1482 | 2185-79 |
| 1483 | 2185-83 |
| 1484 | 2185-85 |
| 1485 | 2185-86 |
| 1486 | 2185-87 |
| 1487 | 2185-89 |
| 1488 | 2185-90 |
| 1489 | 2185-92 |
| 1490 | 2185-93 |
| 1491 | 2185-94 |
| 1492 | 2185-96 |
| 1493 | 2187-02 |
| 1494 | 2187-06 |
| 1495 | 2187-08 |
| 1496 | 2187-11 |
| 1497 | 2187-12 |
| 1498 | 2187-15 |
| 1499 | 2187-16 |
| 1500 | 2187-19 |
| 1501 | 2187-22 |
| 1502 | 2187-26 |
| 1503 | 2187-27 |
| 1504 | 2187-28 |
| 1505 | 2187-29 |
| 1506 | 2187-30 |
| 1507 | 2187-34 |
| 1508 | 2187-35 |
| 1509 | 2187-37 |
| 1510 | 2187-38 |
| 1511 | 2187-39 |
| 1512 | 2187-40 |
| 1513 | 2187-41 |
| 1514 | 2187-42 |
| 1515 | 2187-44 |
| 1516 | 2187-46 |
| 1517 | 2187-48 |
| 1518 | 2187-50 |
| 1519 | 2187-51 |
| 1520 | 2187-52 |
| 1521 | 2187-54 |
| 1522 | 2187-55 |
| 1523 | 2187-56 |
| 1524 | 2187-57 |
| 1525 | 2187-58 |
| 1526 | 2187-60 |
| 1527 | 2187-61 |
| 1528 | 2187-62 |
| 1529 | 2187-63 |
| 1530 | 2187-70 |
| 1531 | 2187-71 |
| 1532 | 2187-72 |
| 1533 | 2187-73 |
| 1534 | 2187-80 |
| 1535 | 2187-84 |
| 1536 | 2187-85 |
| 1537 | 2187-86 |
| 1538 | 2187-87 |
| 1539 | 2187-88 |
| 1540 | 2187-91 |
| 1541 | 2187-94 |
| 1542 | 2187-96 |
| 1543 | 2188-04 |
| 1544 | 2188-08 |
| 1545 | 2188-09 |
| 1546 | 2188-11 |
| 1547 | 2188-18 |
| 1548 | 2188-20 |
| 1549 | 2188-21 |
| 1550 | 2188-23 |
| 1551 | 2188-25 |
| 1552 | 2188-31 |
| 1553 | 2188-37 |
| 1554 | 2188-38 |
| 1555 | 2188-42 |
| 1556 | 2188-43 |
| 1557 | 2188-44 |
| 1558 | 2188-47 |
| 1559 | 2188-50 |
| 1560 | 2188-53 |
| 1561 | 2188-55 |
| 1562 | 2188-57 |
| 1563 | 2188-59 |
| 1564 | 2188-61 |

TABLE II-continued represents a variety of flea HMT nucleic acid molecules of the present invention.

| SEQ ID NO: | Name |
|---|---|
| 1565 | 2188-64 |
| 1566 | 2188-69 |
| 1567 | 2188-70 |
| 1568 | 2188-71 |
| 1569 | 2188-73 |
| 1570 | 2188-76 |
| 1571 | 2188-79 |
| 1572 | 2188-84 |
| 1573 | 2188-85 |
| 1574 | 2188-87 |
| 1575 | 2188-88 |
| 1576 | 2188-89 |
| 1577 | 2188-94 |
| 1578 | 2188-95 |
| 1579 | 2188-96 |
| 1580 | 2189-02 |
| 1581 | 2189-03 |
| 1582 | 2189-04 |
| 1583 | 2189-05 |
| 1584 | 2189-06 |
| 1585 | 2189-07 |
| 1586 | 2189-09 |
| 1587 | 2189-10 |
| 1588 | 2189-11 |
| 1589 | 2189-12 |
| 1590 | 2189-14 |
| 1591 | 2189-15 |
| 1592 | 2189-16 |
| 1593 | 2189-18 |
| 1594 | 2189-19 |
| 1595 | 2189-20 |
| 1596 | 2189-22 |
| 1597 | 2189-23 |
| 1598 | 2189-24 |
| 1599 | 2189-25 |
| 1600 | 2189-26 |
| 1601 | 2189-27 |
| 1602 | 2189-28 |
| 1603 | 2189-29 |
| 1604 | 2189-30 |
| 1605 | 2189-32 |
| 1606 | 2189-33 |
| 1607 | 2189-34 |
| 1608 | 2189-35 |
| 1609 | 2189-36 |
| 1610 | 2189-37 |
| 1611 | 2189-38 |
| 1612 | 2189-40 |
| 1613 | 2189-41 |
| 1614 | 2189-43 |
| 1615 | 2189-44 |
| 1616 | 2189-46 |
| 1617 | 2189-47 |
| 1618 | 2189-49 |
| 1619 | 2189-50 |
| 1620 | 2189-52 |
| 1621 | 2189-54 |
| 1622 | 2189-58 |
| 1623 | 2189-59 |
| 1624 | 2189-60 |
| 1625 | 2189-61 |
| 1626 | 2189-62 |
| 1627 | 2189-64 |
| 1628 | 2189-68 |
| 1629 | 2189-72 |
| 1630 | 2189-77 |
| 1631 | 2189-78 |
| 1632 | 2189-79 |
| 1633 | 2189-80 |
| 1634 | 2189-82 |
| 1635 | 2189-88 |
| 1636 | 2189-93 |
| 1637 | 2189-95 |
| 1638 | 2191-05 |
| 1639 | 2191-06 |
| 1640 | 2191-10 |
| 1641 | 2191-11 |
| 1642 | 2191-13 |
| 1643 | 2191-14 |
| 1644 | 2191-15 |
| 1645 | 2191-16 |
| 1646 | 2191-19 |
| 1647 | 2191-21 |
| 1648 | 2191-26 |
| 1649 | 2191-30 |
| 1650 | 2191-31 |
| 1651 | 2191-32 |
| 1652 | 2191-36 |
| 1653 | 2191-37 |
| 1654 | 2191-39 |
| 1655 | 2191-40 |
| 1656 | 2191-42 |
| 1657 | 2191-43 |
| 1658 | 2191-45 |
| 1659 | 2191-48 |
| 1660 | 2191-49 |
| 1661 | 2191-50 |
| 1662 | 2191-54 |
| 1663 | 2191-55 |
| 1664 | 2191-56 |
| 1665 | 2191-61 |
| 1666 | 2191-62 |
| 1667 | 2191-64 |
| 1668 | 2191-65 |
| 1669 | 2191-70 |
| 1670 | 2191-71 |
| 1671 | 2191-74 |
| 1672 | 2191-75 |
| 1673 | 2191-80 |
| 1674 | 2191-84 |
| 1675 | 2191-86 |
| 1676 | 2191-89 |
| 1677 | 2191-91 |
| 1678 | 2191-93 |
| 1679 | 2191-95 |
| 1680 | 2192-04 |
| 1681 | 2192-05 |
| 1682 | 2192-10 |
| 1683 | 2192-11 |
| 1684 | 2192-13 |
| 1685 | 2192-16 |
| 1686 | 2192-18 |
| 1687 | 2192-19 |
| 1688 | 2192-20 |
| 1689 | 2192-21 |
| 1690 | 2192-24 |
| 1691 | 2192-27 |
| 1692 | 2192-32 |
| 1693 | 2192-33 |
| 1694 | 2192-34 |
| 1695 | 2192-39 |
| 1696 | 2192-40 |
| 1697 | 2192-41 |
| 1698 | 2192-45 |
| 1699 | 2192-48 |
| 1700 | 2192-49 |
| 1701 | 2192-51 |
| 1702 | 2192-52 |
| 1703 | 2192-54 |
| 1704 | 2192-55 |
| 1705 | 2192-56 |
| 1706 | 2192-57 |
| 1707 | 2192-58 |
| 1708 | 2192-61 |
| 1709 | 2192-62 |
| 1710 | 2192-64 |
| 1711 | 2192-65 |
| 1712 | 2192-67 |
| 1713 | 2192-73 |
| 1714 | 2192-75 |

TABLE II-continued represents a variety of flea HMT nucleic acid molecules of the present invention.

| SEQ ID NO: | Name |
|---|---|
| 1715 | 2192-76 |
| 1716 | 2192-80 |
| 1717 | 2192-81 |
| 1718 | 2192-83 |
| 1719 | 2192-84 |
| 1720 | 2192-87 |
| 1721 | 2192-89 |
| 1722 | 2192-90 |
| 1723 | 2192-92 |
| 1724 | 2192-93 |
| 1725 | 2192-95 |
| 1726 | 2193-02 |
| 1727 | 2193-05 |
| 1728 | 2193-06 |
| 1729 | 2193-07 |
| 1730 | 2193-08 |
| 1731 | 2193-09 |
| 1732 | 2193-11 |
| 1733 | 2193-12 |
| 1734 | 2193-13 |
| 1735 | 2193-14 |
| 1736 | 2193-15 |
| 1737 | 2193-16 |
| 1738 | 2193-19 |
| 1739 | 2193-20 |
| 1740 | 2193-21 |
| 1741 | 2193-22 |
| 1742 | 2193-23 |
| 1743 | 2193-26 |
| 1744 | 2193-28 |
| 1745 | 2193-30 |
| 1746 | 2193-32 |
| 1747 | 2193-33 |
| 1748 | 2193-34 |
| 1749 | 2193-35 |
| 1750 | 2193-38 |
| 1751 | 2193-40 |
| 1752 | 2193-41 |
| 1753 | 2193-42 |
| 1754 | 2193-44 |
| 1755 | 2193-46 |
| 1756 | 2193-48 |
| 1757 | 2193-55 |
| 1758 | 2193-57 |
| 1759 | 2193-58 |
| 1760 | 2193-59 |
| 1761 | 2193-62 |
| 1762 | 2193-63 |
| 1763 | 2193-64 |
| 1764 | 2193-66 |
| 1765 | 2193-68 |
| 1766 | 2193-69 |
| 1767 | 2193-70 |
| 1768 | 2193-72 |
| 1769 | 2193-73 |
| 1770 | 2193-74 |
| 1771 | 2193-76 |
| 1772 | 2193-78 |
| 1773 | 2193-81 |
| 1774 | 2193-82 |
| 1775 | 2193-83 |
| 1776 | 2193-84 |
| 1777 | 2193-85 |
| 1778 | 2193-86 |
| 1779 | 2193-87 |
| 1780 | 2193-88 |
| 1781 | 2193-91 |
| 1782 | 2194-02 |
| 1783 | 2194-03 |
| 1784 | 2194-04 |
| 1785 | 2194-05 |
| 1786 | 2194-06 |
| 1787 | 2194-08 |
| 1788 | 2194-10 |
| 1789 | 2194-11 |
| 1790 | 2194-12 |
| 1791 | 2194-15 |
| 1792 | 2194-19 |
| 1793 | 2194-21 |
| 1794 | 2194-25 |
| 1795 | 2194-26 |
| 1796 | 2194-31 |
| 1797 | 2194-33 |
| 1798 | 2194-34 |
| 1799 | 2194-36 |
| 1800 | 2194-44 |
| 1801 | 2194-45 |
| 1802 | 2194-46 |
| 1803 | 2194-47 |
| 1804 | 2194-48 |
| 1805 | 2194-49 |
| 1806 | 2194-53 |
| 1807 | 2194-54 |
| 1808 | 2194-56 |
| 1809 | 2194-57 |
| 1810 | 2194-58 |
| 1811 | 2194-59 |
| 1812 | 2194-60 |
| 1813 | 2194-61 |
| 1814 | 2194-64 |
| 1815 | 2194-65 |
| 1816 | 2194-66 |
| 1817 | 2194-67 |
| 1818 | 2194-68 |
| 1819 | 2194-70 |
| 1820 | 2194-71 |
| 1821 | 2194-73 |
| 1822 | 2194-74 |
| 1823 | 2194-76 |
| 1824 | 2194-77 |
| 1825 | 2194-79 |
| 1826 | 2194-80 |
| 1827 | 2194-82 |
| 1828 | 2194-87 |
| 1829 | 2194-89 |
| 1830 | 2194-90 |
| 1831 | 2194-91 |
| 1832 | 2194-94 |
| 1833 | 2195-03 |
| 1834 | 2195-04 |
| 1835 | 2195-13 |
| 1836 | 2195-18 |
| 1837 | 2195-19 |
| 1838 | 2195-20 |
| 1839 | 2195-21 |
| 1840 | 2195-23 |
| 1841 | 2195-25 |
| 1842 | 2195-27 |
| 1843 | 2195-29 |
| 1844 | 2195-32 |
| 1845 | 2195-33 |
| 1846 | 2195-35 |
| 1847 | 2195-36 |
| 1848 | 2195-37 |
| 1849 | 2195-38 |
| 1850 | 2195-39 |
| 1851 | 2195-41 |
| 1852 | 2195-42 |
| 1853 | 2195-43 |
| 1854 | 2195-44 |
| 1855 | 2195-46 |
| 1856 | 2195-48 |
| 1857 | 2195-50 |
| 1858 | 2195-52 |
| 1859 | 2195-56 |
| 1860 | 2195-58 |
| 1861 | 2195-59 |
| 1862 | 2195-62 |
| 1863 | 2195-63 |
| 1864 | 2195-64 |

TABLE II-continued represents a variety of flea HMT nucleic acid molecules of the present invention.

| SEQ ID NO: | Name |
|---|---|
| 1865 | 2195-65 |
| 1866 | 2195-68 |
| 1867 | 2195-70 |
| 1868 | 2195-71 |
| 1869 | 2195-74 |
| 1870 | 2195-75 |
| 1871 | 2195-77 |
| 1872 | 2195-78 |
| 1873 | 2195-79 |
| 1874 | 2195-81 |
| 1875 | 2195-82 |
| 1876 | 2195-87 |
| 1877 | 2195-88 |
| 1878 | 2195-89 |
| 1879 | 2195-90 |
| 1880 | 2195-91 |
| 1881 | 2195-93 |
| 1882 | 2195-96 |
| 1883 | 2196-02 |
| 1884 | 2196-05 |
| 1885 | 2196-06 |
| 1886 | 2196-08 |
| 1887 | 2196-09 |
| 1888 | 2196-11 |
| 1889 | 2196-15 |
| 1890 | 2196-16 |
| 1891 | 2196-17 |
| 1892 | 2196-23 |
| 1893 | 2196-25 |
| 1894 | 2196-28 |
| 1895 | 2196-32 |
| 1896 | 2196-33 |
| 1897 | 2196-34 |
| 1898 | 2196-35 |
| 1899 | 2196-36 |
| 1900 | 2196-38 |
| 1901 | 2196-39 |
| 1902 | 2196-40 |
| 1903 | 2196-41 |
| 1904 | 2196-45 |
| 1905 | 2196-49 |
| 1906 | 2196-51 |
| 1907 | 2196-55 |
| 1908 | 2196-56 |
| 1909 | 2196-57 |
| 1910 | 2196-58 |
| 1911 | 2196-66 |
| 1912 | 2196-67 |
| 1913 | 2196-68 |
| 1914 | 2196-73 |
| 1915 | 2196-77 |
| 1916 | 2196-80 |
| 1917 | 2196-87 |
| 1918 | 2196-89 |
| 1919 | 2196-91 |
| 1920 | 2196-92 |
| 1921 | 2196-93 |
| 1922 | 2196-94 |
| 1923 | 2196-96 |
| 1924 | 2197-02 |
| 1925 | 2197-04 |
| 1926 | 2197-05 |
| 1927 | 2197-06 |
| 1928 | 2197-07 |
| 1929 | 2197-09 |
| 1930 | 2197-10 |
| 1931 | 2197-11 |
| 1932 | 2197-12 |
| 1933 | 2197-13 |
| 1934 | 2197-15 |
| 1935 | 2197-16 |
| 1936 | 2197-19 |
| 1937 | 2197-20 |
| 1938 | 2197-27 |
| 1939 | 2197-29 |
| 1940 | 2197-30 |
| 1941 | 2197-31 |
| 1942 | 2197-35 |
| 1943 | 2197-36 |
| 1944 | 2197-37 |
| 1945 | 2197-38 |
| 1946 | 2197-39 |
| 1947 | 2197-40 |
| 1948 | 2197-41 |
| 1949 | 2197-43 |
| 1950 | 2197-44 |
| 1951 | 2197-45 |
| 1952 | 2197-48 |
| 1953 | 2197-49 |
| 1954 | 2197-52 |
| 1955 | 2197-55 |
| 1956 | 2197-56 |
| 1957 | 2197-57 |
| 1958 | 2197-61 |
| 1959 | 2197-62 |
| 1960 | 2197-63 |
| 1961 | 2197-65 |
| 1962 | 2197-66 |
| 1963 | 2197-67 |
| 1964 | 2197-69 |
| 1965 | 2197-71 |
| 1966 | 2197-74 |
| 1967 | 2197-75 |
| 1968 | 2197-76 |
| 1969 | 2197-77 |
| 1970 | 2197-79 |
| 1971 | 2197-82 |
| 1972 | 2197-83 |
| 1973 | 2197-84 |
| 1974 | 2197-85 |
| 1975 | 2197-87 |
| 1976 | 2197-88 |
| 1977 | 2197-89 |
| 1978 | 2197-94 |
| 1979 | 2197-96 |
| 1980 | 2202-18 |
| 1981 | 2202-19 |
| 1982 | 2202-22 |
| 1983 | 2202-25 |
| 1984 | 2202-28 |
| 1985 | 2202-30 |
| 1986 | 2202-31 |
| 1987 | 2202-32 |
| 1988 | 2202-38 |
| 1989 | 2202-44 |
| 1990 | 2202-46 |
| 1991 | 2202-55 |
| 1992 | 2202-64 |
| 1993 | 2202-66 |
| 1994 | 2202-67 |
| 1995 | 2202-68 |
| 1996 | 2202-71 |
| 1997 | 2202-72 |
| 1998 | 2202-73 |
| 1999 | 2202-04 |
| 2000 | 2202-87 |
| 2001 | 2202-93 |
| 2002 | 2202-94 |
| 2003 | 2203-12 |
| 2004 | 2203-20 |
| 2005 | 2203-24 |
| 2006 | 2202-26 |
| 2007 | 2202-30 |
| 2008 | 2202-52 |
| 2009 | 2202-74 |
| 2010 | 2202-78 |
| 2011 | 2202-87 |
| 2012 | 2202-93 |
| 2013 | 2202-94 |
| 2014 | 2204-02 |

TABLE II-continued represents a variety of flea HMT nucleic acid molecules of the present invention.

| SEQ ID NO: | Name |
| --- | --- |
| 2015 | 2204-08 |
| 2016 | 2204-12 |
| 2017 | 2204-14 |
| 2018 | 2204-42 |
| 2019 | 2204-43 |
| 2020 | 2204-49 |
| 2021 | 2204-51 |
| 2022 | 2204-53 |
| 2023 | 2204-54 |
| 2024 | 2204-59 |
| 2025 | 2204-60 |
| 2026 | 2204-61 |
| 2027 | 2204-70 |
| 2028 | 2204-71 |
| 2029 | 2204-73 |
| 2030 | 2204-74 |
| 2031 | 2204-78 |
| 2032 | 2204-83 |
| 2033 | 2204-90 |
| 2034 | 2205-05 |
| 2035 | 2205-11 |
| 2036 | 2205-13 |
| 2037 | 2205-21 |
| 2038 | 2205-22 |
| 2039 | 2205-39 |
| 2040 | 2205-42 |
| 2041 | 2205-44 |
| 2042 | 2205-81 |
| 2043 | 2205-88 |
| 2044 | 2205-94 |
| 2045 | 2229-15 |
| 2046 | 2229-21 |
| 2047 | 2229-23 |
| 2048 | 2229-26 |
| 2049 | 2229-28 |
| 2050 | 2229-30 |
| 2051 | 2229-32 |
| 2052 | 2229-43 |
| 2053 | 2229-52 |
| 2054 | 2229-66 |
| 2055 | 2229-85 |
| 2056 | 2230-17 |
| 2057 | 2230-18 |
| 2058 | 2230-25 |
| 2059 | 2230-29 |
| 2060 | 2230-32 |
| 2061 | 2230-34 |
| 2062 | 2230-46 |
| 2063 | 2230-47 |
| 2064 | 2230-58 |
| 2065 | 2230-65 |
| 2066 | 2230-73 |
| 2067 | 2230-74 |
| 2068 | 2230-95 |
| 2069 | 2231-04 |
| 2070 | 2231-13 |
| 2071 | 2231-16 |
| 2072 | 2231-21 |
| 2073 | 2231-25 |
| 2074 | 2231-28 |
| 2075 | 2231-48 |
| 2076 | 2231-54 |
| 2077 | 2231-58 |
| 2078 | 2231-61 |
| 2079 | 2231-69 |
| 2080 | 2231-93 |
| 2081 | 2232-17 |
| 2082 | 2232-20 |
| 2083 | 2232-26 |
| 2084 | 2232-29 |
| 2085 | 2232-36 |
| 2086 | 2232-37 |
| 2087 | 2232-45 |
| 2088 | 2232-47 |
| 2089 | 2232-48 |
| 2090 | 2232-53 |
| 2091 | 2232-62 |
| 2092 | 2232-75 |
| 2093 | 2232-76 |
| 2094 | 2232-88 |
| 2095 | 2232-89 |
| 2096 | 2232-90 |
| 2097 | 2232-92 |
| 2098 | 2232-93 |
| 2099 | 2232-94 |
| 2100 | 2233-07 |
| 2101 | 2233-15 |
| 2102 | 2233-17 |
| 2103 | 2233-23 |
| 2104 | 2233-26 |
| 2105 | 2233-30 |
| 2106 | 2233-31 |
| 2107 | 2233-34 |
| 2108 | 2233-36 |
| 2109 | 2233-37 |
| 2110 | 2233-43 |
| 2111 | 2233-44 |
| 2112 | 2233-49 |
| 2113 | 2233-50 |
| 2114 | 2233-52 |
| 2115 | 2233-62 |
| 2116 | 2233-73 |
| 2117 | 2233-76 |
| 2118 | 2233-78 |
| 2119 | 2233-79 |
| 2120 | 2233-82 |
| 2121 | 2233-88 |
| 2122 | 2234-04 |
| 2123 | 2234-13 |
| 2124 | 2234-16 |
| 2125 | 2234-22 |
| 2126 | 2234-24 |
| 2127 | 2234-38 |
| 2128 | 2234-41 |
| 2129 | 2234-45 |
| 2130 | 2234-48 |
| 2131 | 2234-49 |
| 2132 | 2234-59 |
| 2133 | 2234-69 |
| 2134 | 2234-83 |
| 2135 | 2234-84 |
| 2136 | 2234-87 |
| 2137 | 2234-92 |
| 2138 | 2234-95 |
| 2139 | 2240-15 |
| 2140 | 2240-16 |
| 2141 | 2240-25 |
| 2142 | 2240-27 |
| 2143 | 2240-30 |
| 2144 | 2240-32 |
| 2145 | 2240-41 |
| 2146 | 2240-45 |
| 2147 | 2240-50 |
| 2148 | 2240-56 |
| 2149 | 2240-65 |
| 2150 | 2240-68 |
| 2151 | 2240-73 |
| 2152 | 2240-78 |
| 2153 | 2240-79 |
| 2154 | 2240-81 |
| 2155 | 2240-84 |
| 2156 | 2240-96 |
| 2157 | 2241-06 |
| 2158 | 2241-20 |
| 2159 | 2241-32 |
| 2160 | 2241-33 |
| 2161 | 2241-34 |
| 2162 | 2241-43 |
| 2163 | 2241-46 |
| 2164 | 2241-48 |

TABLE II-continued represents a variety of flea HMT nucleic acid molecules of the present invention.

| SEQ ID NO: | Name |
|---|---|
| 2165 | 2241-50 |
| 2166 | 2241-53 |
| 2167 | 2241-67 |
| 2168 | 2241-71 |
| 2169 | 2241-75 |
| 2170 | 2241-77 |
| 2171 | 2241-79 |
| 2172 | 2241-88 |
| 2173 | 2241-96 |
| 2174 | 2243-05 |
| 2175 | 2243-07 |
| 2176 | 2243-16 |
| 2177 | 2243-23 |
| 2178 | 2243-26 |
| 2179 | 2243-34 |
| 2180 | 2243-40 |
| 2181 | 2243-42 |
| 2182 | 2243-58 |
| 2183 | 2243-60 |
| 2184 | 2243-65 |
| 2185 | 2243-70 |
| 2186 | 2243-80 |
| 2187 | 2243-84 |
| 2188 | 2244-04 |
| 2189 | 2244-07 |
| 2190 | 2244-09 |
| 2191 | 2244-10 |
| 2192 | 2244-17 |
| 2193 | 2244-18 |
| 2194 | 2244-20 |
| 2195 | 2244-22 |
| 2196 | 2244-24 |
| 2197 | 2244-28 |
| 2198 | 2244-34 |
| 2299 | 2244-37 |
| 2200 | 2244-39 |
| 2201 | 2244-41 |
| 2202 | 2244-46 |
| 2203 | 2244-50 |
| 2204 | 2244-51 |
| 2205 | 2244-56 |
| 2206 | 2244-60 |
| 2207 | 2244-67 |
| 2208 | 2244-70 |
| 2209 | 2244-72 |
| 2210 | 2244-73 |
| 2211 | 2244-79 |
| 2212 | 2244-81 |
| 2213 | 2244-85 |
| 2214 | 2244-88 |
| 2215 | 2244-89 |
| 2216 | 2244-90 |
| 2217 | 2244-92 |
| 2218 | 2244-93 |
| 2219 | 2244-94 |
| 2220 | 2244-95 |
| 2221 | 2244-96 |
| 2222 | 2253-03 |
| 2223 | 2253-09 |
| 2224 | 2253-10 |
| 2225 | 2253-15 |
| 2226 | 2253-17 |
| 2227 | 2253-25 |
| 2228 | 2253-26 |
| 2229 | 2253-29 |
| 2230 | 2253-31 |
| 2231 | 2253-34 |
| 2232 | 2253-45 |
| 2233 | 2253-47 |
| 2234 | 2253-48 |
| 2235 | 2253-49 |
| 2236 | 2253-51 |
| 2237 | 2253-57 |
| 2238 | 2253-64 |
| 2239 | 2253-69 |
| 2240 | 2253-71 |
| 2241 | 2253-72 |
| 2242 | 2253-74 |
| 2243 | 2253-75 |
| 2244 | 2253-76 |
| 2245 | 2253-77 |
| 2246 | 2253-85 |
| 2247 | 2253-91 |
| 2248 | 2253-93 |
| 2249 | 2254-02 |
| 2250 | 2254-03 |
| 2251 | 2254-05 |
| 2252 | 2254-09 |
| 2253 | 2254-11 |
| 2254 | 2254-19 |
| 2255 | 2254-20 |
| 2256 | 2254-22 |
| 2257 | 2254-34 |
| 2258 | 2254-42 |
| 2259 | 2254-44 |
| 2260 | 2254-46 |
| 2261 | 2254-49 |
| 2262 | 2254-50 |
| 2263 | 2254-52 |
| 2264 | 2254-59 |
| 2265 | 2254-61 |
| 2266 | 2254-64 |
| 2267 | 2254-73 |
| 2268 | 2254-75 |
| 2269 | 2254-77 |
| 2270 | 2254-78 |
| 2271 | 2254-81 |
| 2272 | 2254-82 |
| 2273 | 2254-89 |
| 2274 | 2254-90 |
| 2275 | 2254-94 |
| 2276 | 2255-06 |
| 2277 | 2255-09 |
| 2278 | 2255-11 |
| 2279 | 2255-26 |
| 2280 | 2255-27 |
| 2281 | 2255-29 |
| 2282 | 2255-38 |
| 2283 | 2255-44 |
| 2284 | 2255-48 |
| 2285 | 2255-53 |
| 2286 | 2255-65 |
| 2287 | 2255-74 |
| 2288 | 2255-78 |
| 2289 | 2255-81 |
| 2290 | 2255-83 |
| 2291 | 2255-84 |
| 2292 | 2255-87 |
| 2293 | 2255-92 |
| 2294 | 2255-93 |
| 2295 | 2256-02 |
| 2296 | 2256-09 |
| 2297 | 2256-10 |
| 2298 | 2256-25 |
| 2299 | 2256-37 |
| 2300 | 2256-51 |
| 2301 | 2256-53 |
| 2302 | 2256-56 |
| 2303 | 2256-60 |
| 2304 | 2256-63 |
| 2305 | 2256-66 |
| 2306 | 2256-68 |
| 2307 | 2256-71 |
| 2308 | 2256-74 |
| 2309 | 2256-81 |
| 2310 | 2256-83 |
| 2311 | 2256-84 |
| 2312 | 2256-88 |
| 2313 | 2256-95 |

In one embodiment, a gene or other nucleic acid molecule of the present invention can be an allelic variant that includes a similar but not identical sequence to a *C. felis* nucleic acid sequence of Table I and/or Table II or a complement thereof. For example, an allelic variant of a *C. felis* gene including SEQ ID NO:1 is a gene that occurs at essentially the same locus (or loci) in the genome as the gene including SEQ ID NO:1, but which, due to natural variations caused by, for example, mutation or recombination, has a similar but not identical sequence. Because natural selection typically selects against alterations that affect function, allelic variants (i.e. alleles corresponding to, or of, cited nucleic acid sequences) usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to occur naturally within a given flea such as *C. felis*, since the genome is diploid, and sexual reproduction will result in the reassortment of alleles.

In one embodiment of the present invention, isolated HMT and HNC proteins are encoded by nucleic acid molecules that hybridize under stringent hybridization conditions to genes or other nucleic acid molecules encoding flea HMT and HNC proteins, respectively. The minimal size of HMT and HNC proteins of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the flea HMT or HNC nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding a flea HMT or HNC protein is typically at least about 12 to about 15 nucleotides in length if the nucleic acid molecule is GC-rich and at least about 15 to about 17 bases in length if it is AT-rich. The minimal size of a nucleic acid molecule used to encode an HMT or HNC protein homologue of the present invention is from to about 12 to about 18 nucleotides in length. Thus, the minimal size of HMT or HNC protein homologues of the present invention is from about 4 to about 6 amino acids in length. There is no limit, other than a practical limit, on the maximal size of a nucleic acid molecule encoding a flea HMT or HNC protein of the present invention because a nucleic acid molecule of the present invention can include a portion of a gene, an entire gene, or multiple genes. The preferred size of a protein encoded by a nucleic acid molecule of the present invention depends on whether a full-length, fusion, multivalent, or functional portion of such a protein is desired.

Stringent hybridization conditions are determined based on defined physical properties of the gene to which the nucleic acid molecule is being hybridized, and can be defined mathematically Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267-284, each of which is incorporated by reference herein in its entirety. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarily between the two strands:

$$T_m = 81.5° C. + 16.6 \log M + 0.41(\% G+C) - 500/n - 0.61(\% \text{ formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base pairs for hybrids greater than about 150 bp, and $T_d$ decreases about 5° C. for each mismatched base pair for hybrids below about 50 bp. Conditions for hybrids between about 50 and about 150 base pairs can be determined empirically and without undue experimentation using standard laboratory procedures well known to those skilled in the art. These simple procedures allow one skilled in the art to set the hybridization conditions (by altering, for example, the salt concentration, the helix destabilizing compound concentration or the temperature) so that only nucleic acid hybrids with greater than a specified % base pair mismatch will hybridize. Stringent hybridization conditions are commonly understood by those skilled in the art to be those experimental conditions that will allow less than or equal to about 30% base pair mismatch (i.e., at least about 70% identity). Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and to similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under conditions that would allow less than or equal to 30% pair mismatch with a flea nucleic acid molecule of about 150 bp in length or greater, the following conditions could preferably be used. The average G+C content of flea DNA is about 37%, as calculated from known flea nucleic acid sequences. The unknown nucleic acid molecules would be attached to a support membrane, and the 150 bp probe would be labeled, e.g. with a radioactive tag. The hybridization reaction could be carried out in a solution comprising 2× SSC in the absence of helix destabilizing compounds, at a temperature of about 37° C. (low stringency conditions). Solutions of differing concentrations of SSC can be made by one of skill in the art by diluting a stock solution of 20× SSC (175.3 gram NaCl and about 88.2 gram sodium citrate in 1 liter of water, pH 7) to obtain the desired concentration of SSC. The skilled artisan would calculate the washing conditions required to allow up to 30% base pair mismatch. For example, in a wash solution comprising 1×SSC in the absence of helix destabilizing compounds, the $T_m$ of perfect hybrids would be about 77° C.:

$$81.5° C.+16.6 \log(0.15 M)+(0.41\times0.37)-(500/150)-(0.61\times0)=77.5° C.$$

Thus, to achieve hybridization with nucleic acid molecules having about 30% base pair mismatch, hybridization washes would be carried out at a temperature of less than or equal to 47.5° C. It is thus within the skill of one in the art to calculate additional hybridization temperatures based on the desired percentage base pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base pair mismatch will not vary significantly from 47.5° C.

Furthermore, it is known in the art that there are commercially available computer programs for determining the degree of similarity between two nucleic acid or protein sequences. These computer programs include various known methods to determine the percentage identity and the number and length of gaps between hybrid nucleic acid molecules or proteins. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, the SeqLab® Wisconsin Package™ Version 10.0-UNIX sequence analysis software (hereinafter referred to as "SeqLab"), available from Genetics Computer Group, Madison, Wis.; and DNAsis® sequence analysis software, version 2.0, available from Hitachi Software, San Bruno, Calif. Such software programs represent a collection of algorithms paired with a graphical user interface for using the algorithms. The DNAsis version 2.0 software and SeqLab Wisconsin Package Version 10.0-UNIX software, for example, employ a particular algorithm, the Needleman-Wunsch algorithm to perform pair-wise comparisons between two sequences to yield a percentage identity score, see Needleman, S. B. and Wunch, C. D., 1970, *J. Mol. Biol.*, 48, 443, which is incorporated herein by reference in its entirety. Such algorithms, including the Needleman-Wunsch algorithm, are commonly used by those skilled in the nucleic acid and amino acid sequencing art to compare sequences. A preferred method to determine percent identity among amino acid sequences and also among nucleic acid sequences includes using the Needleman-Wunsch algorithm, available in the SeqLab Wisconsin Package Version 10.0-UNIX software (hereinafter "SeqLab"), using the Pairwise Comparison/Gap function with the nwsgapdna.cmp scoring matrix, the gap creation penalty and the gap extension penalties set at default values, and the gap shift limits set at maximum (hereinafter referred to as "SeqLab default parameters"). An additional preferred method to determine percent identity among amino acid sequences and also among nucleic acid sequences includes using the Higgins-Sharp algorithm, available in the DNAsis version 2.0 software (hereinafter "DNAsis"), with the gap penalty set at 5, the number of top diagonals set at 5, the fixed gap penalty set at 10, the k-tuple set at 2, the window size set at 5, and the floating gap penalty set at 10. A particularly preferred method to determine percent identity among amino acid sequences and also among nucleic acid sequences includes using the Needleman-Wunsch algorithm available in the SeqLab software, using the SeqLab default parameters.

A preferred flea HMT and/or HNC protein includes a protein encoded by a nucleic acid molecule that hybridizes under conditions that preferably allow less than or equal to 30% base pair mismatch, preferably under conditions that allow less than or equal to 25% base pair mismatch, preferably under conditions that allow less than or equal to 20% base pair mismatch, preferably under conditions that allow less than or equal to 15% base pair mismatch, preferably under conditions that allow less than or equal to 10% base pair mismatch and preferably under conditions that allow less than or equal to 5% base pair mismatch with a nucleic acid molecule selected from the group consisting of a nucleic acid sequence complementary to a nucleic acid sequence of Table I and/or Table II.

Another embodiment of the present invention includes a flea HMT and/or HNC protein encoded by a nucleic acid molecule that hybridizes under conditions comprising, (a) hybridizing in a solution comprising 1×SSC in the absence of helix destabilizing compounds, at a temperature of 37° C. and (b) washing in a solution comprising 1×SSC in the absence of helix destabilizing compounds, at a temperature of 47.50° C., to an isolated nucleic acid molecule selected from the group consisting of a nucleic acid sequence complementary to a nucleic acid sequence of Table I and/or Table II.

Another preferred flea HMT and/or HNC protein of the present invention includes a protein that is encoded by a nucleic acid molecule that is preferably at least 70% identical, preferably at least 75% identical, preferably at least 80% identical, preferably at least 85% identical, preferably at least 90% identical, and preferably at least 95% identical to a nucleic acid molecule having a nucleic acid sequence of Table I and/or Table II; also preferred are fragments (i.e. portions) of such proteins encoded by nucleic acid molecules that are at least 18 nucleotides. Percent identity as used herein is determined using the Compare function by maximum matching within the program DNAsis Version 2.1 using default parameters.

Additional preferred flea HMT and/or HNC proteins of the present invention include proteins having an amino acid sequence encoded by a nucleic acid sequence of Table I and/or Table II, and proteins comprising homologues of a protein encoded by a nucleic acid sequence of Table I and/or Table II, wherein such a homologue comprises at least one epitope that elicits an immune response against a protein encoded by a nucleic acid sequence of Table I and/or Table II.

In one embodiment, a preferred flea HMT or HNC protein comprises an amino acid sequence of at least 6 amino acids, preferably at least 10 amino acids, preferably at least 15 amino acids, preferably at least 20 amino acids, preferably at least 25 amino acids, preferably at least 30 amino acids, preferably at least 35 amino acids, preferably at least 40 amino acids, preferably at least 50 amino acids, preferably at least 100 amino acids, preferably at least 200 amino acids, preferably at least 250 amino acids, preferably at least 300 amino acids, preferably at least 350 amino acids, and preferably at least 375 amino acids. In another embodiment, preferred flea HMT and HNC proteins comprise full-length proteins, i.e., proteins encoded by full-length coding regions, or post-translationally modified proteins thereof, such as mature proteins from which initiating methionine and/or signal sequences or "pro" sequences have been removed.

A fragment of an HMT and/or HNC protein of the present invention preferably comprises at least 5 amino acids, preferably at least 10 amino acids, preferably at least 15 amino acids, preferably at least 20 amino acids, preferably at least 25 amino acids, preferably at least 30 amino acids, preferably at least 35 amino acids, preferably at least 40 amino acids, preferably at least 45 amino acids, preferably at least 50 amino acids, preferably at least 55 amino acids, preferably at least 60 amino acids, preferably at least 65 amino acids, preferably at least 70 amino acids, preferably at least 75 amino acids, preferably at least 80 amino acids, preferably at least 85 amino acids, preferably at least 90 amino acids, preferably at least 95 amino acids, and preferably at least 100 amino acids in length.

In another embodiment, a preferred flea HMT and/or HNC protein of the present invention is encoded by a nucleic acid molecule comprising at least 15 nucleotides, preferably at least 18 nucleotides, preferably at least 20 nucleotides, preferably at least 25 nucleotides, preferably at least 30 nucleotides, preferably at least 40 nucleotides, preferably at least 50 nucleotides, preferably at least 100 nucleotides, preferably at least 150 nucleotides, preferably at least 350 nucleotides, preferably at least 450 nucleotides, preferably at least 550 nucleotides, preferably at least 650 nucleotides, preferably at least 750 nucleotides, preferably at least 1000 nucleotides, and preferably at least 1100 nucleotides in length. In another embodiment, preferred flea HMT and HNC proteins of the present invention are encoded by nucleic acid molecules comprising apparently full-length HMT or HNC coding regions respectively, i.e., nucleic acid molecules encoding an apparently full-length HMT or HNC proteins.

Preferred flea HMT and HNC proteins of the present invention can be used to develop inhibitors that, when administered to an animal in an effective manner, are capable of protecting that animal from flea infestation. In accordance with the present invention, the ability of an inhibitor of the present invention to protect an animal from flea infestation refers to the ability of that protein to, for example, treat, ameliorate and/or prevent infestation caused by fleas. In particular, the phrase "to protect an animal from flea infestation" refers to reducing the potential for flea population expansion on and around the animal (i.e., reducing the flea burden). Preferably, the flea population size is decreased, optimally to an extent that the animal is no longer bothered by fleas. A host animal, as used herein, is an animal from which fleas can feed by attaching to and feeding through the skin of the animal. Fleas, and other ectoparasites, can live on a host animal for an extended period of time or can attach temporarily to an animal in order to feed. At any given time, a certain percentage of a flea population can be on a host animal whereas the remainder can be in the environment of the animal. Such an environment can include not only adult fleas, but also flea eggs and/or flea larvae. The environment can be of any size such that fleas in the environment are able to jump onto and off of a host animal. For example, the environment of an animal can include plants, such as crops, from which fleas infest an animal. As such, it is desirable not only to reduce the flea burden on an animal per se, but also to reduce the flea burden in the environment of the animal.

Suitable fleas to target include any flea that is essentially incapable of causing disease in an animal administered an inhibitor of the present invention. As such, fleas to target include any flea that produces a protein that can be targeted by an inhibitory compound that inhibits a flea HMT or HNC protein function, thereby resulting in the decreased ability of the parasite to cause disease in an animal. Preferred fleas to target include fleas of the following genera: *Ctenocephalides, Cyopsyllus, Diamanus (Oropsylla), Echidnophaga, Nosopsyllus, Pulex, Tunga,* and *Xenopsylla*, with those of the to species *Ctenocephalides canis, Ctenocephalidesfelis, Diamanus montanus, Echidnophaga gallinacea, Nosopsyllusfaciatus, Pulex irritans, Pulex simulans, Tunga penetrans* and *Xenopsylla cheopis* being more preferred, with *C. felis* being preferred. Such fleas are also preferred for the isolation of proteins or nucleic acid molecules of the present invention.

One embodiment of a flea HMT and/or HNC protein of the present invention is a fusion protein that includes a flea HMT and/or HNC protein-containing domain attached to one or more fusion segments. Suitable fusion segments for use with the present invention include, but are not limited to, segments that can: enhance a protein's stability; act as an immunopotentiator to enhance an immune response against a flea HMT and/or HNC protein; and/or assist in purification of a flea HMT and/or HNC protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the flea HMT-containing and/or HNC-containing domain of the protein and can be susceptible to cleavage in order to enable straight-forward recovery of a flea HMT and/or HNC protein. Fusion proteins are preferably produced by culturing a recombinant cell transformed with a fusion nucleic acid molecule that encodes a protein including the fusion segment attached to either the carboxyl and/or amino terminal end of an HMT-containing and/or HNC-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

The present invention also includes mimetopes of flea HMT and/or HNC proteins of the present invention. As used herein, a mimetope of a flea HMT and/or HNC protein of the present invention refers to any compound that is able to mimic the activity of such an HMT and/or HNC protein, often because the mimetope has a structure that mimics the particular HMT and/or HNC protein. Mimetopes can be, but are not limited to: peptides that have been modified to decrease their susceptibility to degradation such as all-D retro peptides; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

Another embodiment of the present invention is an isolated nucleic acid molecule comprising a flea HMT and/or HNC nucleic acid molecule, i.e. a nucleic acid molecule that can be isolated from a HMT cDNA library, from a HNC cDNA library, or from both libraries. As used herein, HMT and HNC nucleic acid molecules has the same meaning as HMT and/or HNC nucleic acid molecule. The identifying characteristics of such nucleic acid molecules are heretofore described. A nucleic acid molecule of the present invention can include an isolated natural flea HMT and/or HNC gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of a HMT and/or HNC nucleic acid molecule of the present invention is from 12 to 18 nucleotides in length.

Suitable and preferred fleas from which to isolate nucleic acid molecules of the present invention are disclosed herein. Particularly preferred HMT and/or HNC nucleic acid molecules include C. felis HMT and/or HNC nucleic acid molecules.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. Isolated flea HMT and/or HNC nucleic acid molecules of the present invention, or homologues thereof, can be isolated from a natural source or produced using recombinant DNA technology (e.g., polymerase chain reaction (PCR) amplification or cloning) or chemical synthesis. Isolated flea HMT and/or HNC nucleic acid molecules, and homologues thereof, can include, for example, natural allelic variants and nucleic acid molecules modified by nucleotide insertions, deletions, substitutions, and/or inversions in a manner such that the modifications do not substantially interfere with the nucleic acid molecule's ability to encode a HMT and/or HNC protein of the present invention.

A flea HMT and/or HNC nucleic acid molecule homologue can be produced using a number of methods known to those skilled in the art, see, for example, Sambrook et al., ibid., is incorporated by reference herein in its entirety. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologues can be selected by hybridization with flea HMT and/or HNC nucleic acid molecules or by screening the function of a protein encoded by the nucleic acid molecule (e.g., ability to elicit an immune response against at least one epitope of a flea HMT or HNC protein or to effect HMT or HNC activity).

An isolated nucleic acid molecule of the present invention can include a nucleic acid sequence that encodes at least one flea HMT or HNC protein of the present invention, examples of such proteins being disclosed herein. Although the phrase "Nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a flea HMT or HNC protein.

A preferred nucleic acid molecule of the present invention, when administered to an animal, is capable of protecting that animal from flea infestation. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein (e.g., an HMT or HNC protein of the present invention), the nucleic acid molecule being delivered to the animal, for example, by direct injection (i.e., as a genetic vaccine) or in a vehicle such as a recombinant virus vaccine or a recombinant cell vaccine.

In one embodiment of the present invention, a preferred flea HMT and/or HNC nucleic acid molecule includes an isolated nucleic acid molecule that hybridizes under conditions that preferably allow less than or equal to 30% base pair mismatch, preferably under conditions that allow less than or equal to 25% base pair mismatch, preferably under conditions that allow less than or equal to 20% base pair mismatch, preferably under conditions that allow less than or equal to 15% base pair mismatch, preferably under conditions that allow less than or equal to 10% base pair mismatch and preferably under conditions that allow less than or equal to 5% base pair mismatch with a nucleic acid molecule of Table I and/or Table II and/or a nucleic acid molecule that is complementary to a nucleic acid molecule of Table I and/or Table II.

Another embodiment of the present invention includes a HMT and/or HNC nucleic acid molecule, wherein said nucleic acid molecule hybridizes, in a solution comprising 1× SSC in the absence of helix destabilizing compounds, at a temperature of 47.5° C., to an isolated nucleic acid molecule a nucleic acid molecule of Table I or Table II and/or a nucleic acid molecule that is complementary to a nucleic acid molecule of Table I or Table II. Additional preferred nucleic acid molecules of the present invention include oligonucleotides of an isolated nucleic acid molecule, wherein said nucleic acid molecule hybridizes, in a solution comprising 1× SSC in the absence of helix destabilizing compounds, at a temperature of 47.5° C., to an isolated nucleic acid molecule of Table I or Table II and/or a nucleic acid molecule that is complementary to a nucleic acid molecule of Table I or Table II, wherein said oligonucleotide comprises at least 18 nucleotides.

Additional preferred flea HMT and/or HNC nucleic acid molecules of the present invention include nucleic acid molecules comprising a nucleic acid sequence that is preferably at least 70%, preferably at least 75%, preferably at least 80% preferably at least 85%, preferably at least 90%, and preferably at least 95% identical to a nucleic acid sequence of Table I or Table II and/or a nucleic acid molecule that is complementary to a nucleic acid molecule of Table I or Table II. Also preferred are oligonucleotides of any of such nucleic acid molecules. Percent identity may be determined using the SeqLab sequence analysis software, using default parameters.

Another preferred nucleic acid molecule of the present invention includes at least a portion of nucleic acid sequence of Table I or Table IT, as well as allelic variants of nucleic acid molecules having these nucleic acid sequences and homologues of nucleic acid molecules having these nucleic acid sequences; preferably such a homologue encodes or is complementary to a nucleic acid molecule that encodes at least one epitope that elicits an immune response against a protein encoded by a nucleic acid molecule of Table I and/or Table II. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

In one embodiment, HMT and/or HNC nucleic acid molecule of the present invention encodes a protein that is at least 70%, preferably at least 75%, preferably at least 80%, preferably at least 85%, preferably at least 90%, preferably at least 95%, preferably at least 98%, and preferably at least 100% identical to a protein encoded by a nucleic acid molecule having a sequence of Table I and/or Table II.

In one embodiment, a HMT and/or HNC nucleic acid molecule of the present invention encodes a protein having an amino acid sequence that is at least 70%, preferably at least 75%, preferably at least 80%, preferably at least 85%, preferably at least 90%, preferably at least 95%, preferably at least 98%, and preferably at least 100% identical to a protein encoded by a nucleic acid molecule having a sequence of Table I and/or Table 11. The present invention also includes a HMT and/or HNC nucleic acid molecule encoding a protein having at least a portion of a protein encoded by a nucleic acid molecule having a sequence of Table I and/or Table II, as well as allelic variants of a nucleic acid molecule encoding a protein having these sequences, including nucleic acid molecules that have been modified to accommodate codon usage properties of the cells in which such nucleic acid molecules are to be expressed.

In another embodiment, a preferred flea HMT and/or HNC nucleic acid molecule of the present invention comprises a nucleic acid molecule comprising at least 15 nucleotides, preferably at least 18 nucleotides, preferably at least 20 nucleotides, preferably at least 25 nucleotides, preferably at least 30 nucleotides, preferably at least 40 nucleotides, preferably at least 50 nucleotides, preferably at least 100 nucleotides, preferably at least 150 nucleotides, preferably at least 350 nucleotides, preferably at least 450 nucleotides, preferably at least 550 nucleotides, preferably at least 650 nucleotides, preferably at least 750 nucleotides, preferably at least 1000 nucleotides, and preferably at least 1100 nucleotides in length.

In another embodiment, a preferred flea HMT and/or HNC nucleic acid molecule encodes a protein comprising at least 5 amino acids, preferably at least 6 amino acids, preferably at least 10 amino acids, preferably at least 15 amino acids, preferably at least 20 amino acids, preferably at least 25 amino acids, preferably at least 30 amino acids, preferably at least 40 amino acids, preferably at least 50 amino acids, preferably at least 100 amino acids, preferably at least 150 amino acids, preferably at least 200 amino acids, preferably at least 300 amino acids, preferably at least 350 amino acids, and preferably at least 350 amino acids in length.

In another embodiment, a preferred flea HMT and/or HNC nucleic acid molecule of the present invention comprises an apparently full-length HMT and/or HNC coding region, i.e., the preferred nucleic acid molecule encodes an apparently full-length HMT and/or HNC protein, or a post-translationally modified protein thereof. In one embodiment, a preferred HMT and/or HNC nucleic acid molecule of the present invention encodes a mature protein.

Knowing the nucleic acid sequences of certain flea HMT and/or HNC nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other flea HMT and/or HNC nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include flea $1^{st}$ instar larvae; $3^{rd}$ instar larvae, wandering larvae, prepupal larvae, pupae and whole adult flea cDNA libraries as well as genomic DNA libraries. Similarly, preferred DNA sources to screen or from which to amplify nucleic acid molecules include flea prepupal cDNA, adult cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising C. felis HMT and/or HNC nucleic acid molecules or other flea HMT and/or HNC nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of preferably 100 to 200 nucleotides. The present invention includes oligonucleotides that can be used as, for example, probes to identify nucleic acid molecules, primers to produce nucleic acid molecules, or therapeutic reagents to inhibit flea HMT and/or HNC protein production or activity (e.g., as antisense, triplex formation, ribozyme and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of flea HMT and/or HNC nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, insect and mammalian cells, and preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences that control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those that function in bacterial, yeast, or insect and mammalian cells, such as, but not limited to, tac, lac, trp, trc, oxy-pro, omp/lpp, rrnB, bacteriophage lambda (such as lambda $P_L$ and lambda $P_R$ and fusions that include such promoters), bacteriophage T7, T7lac, bacteriophage T3, bacteriophage SP6, bacteriophage SP01, metallothionein, alpha-mating factor, *Pichia* alcohol oxidase, alphavirus subgenomic promoter, antibiotic resistance gene, baculovirus, *Heliothis* zea insect virus, vaccinia virus, herpesvirus, raccoon poxvirus, other poxvirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with fleas, such as *C. felis* transcription control sequences.

Suitable and preferred nucleic acid molecules to include in recombinant vectors of the present invention are as disclosed herein. Preferred nucleic acid molecules to include in recombinant vectors, and particularly in recombinant molecules, include nucleic acid molecules having a sequence of Table I and/or Table II.

Recombinant molecules of the present invention may also (a) contain secretory signals (i.e., signal segment nucleic acid sequences) to enable an expressed flea protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include *C. felis* HMT and HNC nucleic acid molecules disclosed herein. Preferred nucleic acid molecules with which to transform a cell include nucleic acid molecules having a sequence of Table I and/or Table II.

Suitable host cells to transform include any cell that can be transformed with a nucleic acid molecule of the present invention. Host cells can be either untransformed cells or cells that are already transformed with at least one nucleic acid molecule (e.g. nucleic acid molecules encoding one or more proteins of the present invention and/or other proteins useful in the production of multivalent vaccines). Host cells of the present invention either can be endogenously (i.e., naturally) capable of producing flea HMT and/or HNC proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, insect and mammalian cells. More preferred host cells include *Salmonella, Escherichia, Bacillus, Caulobacter, Listeria, Saccharomyces, Pichia, Spodoptera, Mycobacteria, Tri-*

*choplusia*, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi; Salmonella typhimurium*, including attenuated strains such as UK-1$_x$3987 and SR-11$_x$4072; Caulobacter; *Pichia; Spodoptera frugiperda; Trichoplusia ni*; BHK cells; MDCK cells; CRFK cells; CV-1 cells; COS cells; Vero cells; and non-tumorigenic mouse myoblast G8 cells (e.g., ATCC CRL 1246). Additional appropriate mammalian cell hosts include other kidney cell lines, other fibroblast cell to lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein. The phrase operatively linked refers to insertion of a nucleic acid molecule into an expression vector in a manner such that the molecule is able to be expressed when transformed into a host cell.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including flea HMT and/or HNC nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated flea HMT and/or HNC proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a flea HMT and/or HNC protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petit plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes. Such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a flea HMT and/or HNC protein of the present invention or a mimetope thereof (e.g., anti-*C. felis* HMT or HNC antibodies). As used herein, the term "selectively binds to" an HMT and/or HNC protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press; Harlow et al., ibid., is incorporated by reference herein in its entirety. An anti-HMT or anti-HNC antibody of the present invention preferably selectively binds to a flea HMT or HNC protein respectively in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce HMT and/or HNC proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from fleas susceptible to treatment by such antibodies and/or (b) as tools to screen expression libraries and/or to recover desired proteins of the present invention from a mixture of proteins and other contaminants. Furthermore, antibodies of the present invention can be used to target cytotoxic agents to fleas in order to directly kill such fleas. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal susceptible to flea infestation, is capable of protecting that animal from flea infestation. Therapeutic compositions of the present invention include at least one of the following protective molecules: an isolated flea HMT and/or HNC protein; a mimetope of an isolated flea HMT and/or HNC protein; an isolated flea HMT and/or HNC nucleic acid molecule; and/or a compound derived from said isolated flea HMT and/or HNC protein that inhibits HMT and/or HNC protein activity. A therapeutic composition of the present invention can further comprise a component selected from the group of an excipient, a carrier, and/or an adjuvant; these components are described further herein. As used herein, a protective molecule or protective compound refers to a compound that, when administered to an animal in an effective manner, is able to treat, ameliorate, and/or prevent flea infestation. Preferred fleas to target are heretofore disclosed. One example of a protective molecule is a vaccine, such as, but not limited to, a naked nucleic acid vaccine, a recombinant virus vaccine, a recombinant cell vaccine, and a recombinant protein vaccine. Another example of a protective molecule is a compound that inhibits HMT and/or HNC protein activity, such as an isolated antibody that selectively binds to a flea HMT and/or HNC protein, a substrate analog of a flea HMT and/or HNC protein, anti-sense-, triplex formation-, ribozyme-, and/or KNA drug-based compounds, or other inorganic or organic molecules that inhibit HMT and/or HNC protein activity. Inhibiting flea HMT and/or HNC protein activity can refer to the ability of a compound to reduce the activity of flea HMT and/or HNC proteins. Inhibiting flea HMT and/or HNC protein activity can also refer to the ability of a compound to reduce the amount of flea HMT and/or HNC protein in a flea.

Another embodiment of the present invention includes a method to reduce a flea infestation in an animal susceptible to flea infestation. Such a method includes the step of administering to the animal a therapeutic molecule comprising a protective compound selected from the group consisting of (a) an isolated flea HMT and/or HNC protein; (b) a mimetope of an isolated flea HMT and/or HNC protein; (c) an isolated flea HMT and/or HNC nucleic acid molecule; and (d) a compound derived from an isolated flea HMT and/or HNC protein that inhibits HMT and/or HNC protein activity.

Therapeutic compositions of the present invention can be administered to any animal susceptible to flea infestation, preferably to mammals, and preferably to dogs, cats, humans, ferrets, horses, cattle, sheep, and other pets, economic food animals, work animals and/or zoo animals. Preferred animals to protect against flea infestation include dogs, cats, humans, and ferrets, with dogs and cats being particularly preferred.

As used herein, the term derived, or the term derived from, refers to a peptide, antibody, mimetope, nucleic acid molecule, or other compound that was obtained from or obtained using a flea HMT and/or HNC protein or nucleic acid molecule of the present invention. Methods to obtain derivatives from a HMT and/or HNC molecule of the present invention are known in the art, and as such include, but are not limited to molecular modeling of HMT and/or HNC proteins to determine active sites, i.e. sites that interact with other molecules, and predicting from these active sites smaller fragments and/or mimetopes that retain and/or mimic these active sites, thereby inhibiting HMT and/or HNC protein activity; screening of peptide or small chemical compound libraries against HMT and/or HNC proteins of the present invention; and screening of polyclonal or monoclonal antibodies to find antibodies that specifically bind HMT and/or HNC proteins of the present invention.

An EMT and/or HNC protein inhibitor of the present invention is identified by its ability to bind to, modify, or otherwise interact with, a flea HMT and/or HNC protein, thereby inhibiting the activity of HMT and/or HNC proteins. Suitable inhibitors of HMT and/or HNC protein activity are compounds that inhibit HMT and/or HNC protein activity in at least one of a variety of ways: (a) by binding to or otherwise interacting with or otherwise modifying HMT and/or HNC protein sites; (b) by binding to the HMT to and/or HNC protein and thus reducing the availability of the HMT and/or HNC protein in solution; and (c) by interacting with other regions of the HMT and/or HNC protein to inhibit HMT and/or HNC protein activity, for example, by allosteric interaction.

Flea HMT and/or HNC protein inhibitors can be used directly as compounds in compositions of the present invention to treat animals as long as such compounds are not harmful to host animals being treated. Preferred HMT and/or HNC protein inhibitors of the present invention include, but are not limited to, flea HMT and/or HNC protein substrate analogs, and other molecules that bind to a flea HMT and/or HNC proteins (e.g., to an allosteric site) in such a manner that the activity of the flea HMT and/or HNC protein is inhibited. An HMT and/or HNC protein substrate analog refers to a compound that interacts with (e.g., binds to, associates with, modifies) the active site of a HMT and/or HNC protein. A preferred HMT and/or HNC protein substrate analog inhibits HMT and/or HNC protein activity. HMT and/or HNC protein substrate analogs can be of any inorganic or organic composition. HMT and/or HNC protein substrate analogs can be, but need not be, structurally similar to a HMT and/or HNC protein natural substrate as long as they can interact with the active site of that HMT and/or HNC protein. HMT and/or HNC protein substrate analogs can be designed using computer-generated structures of HMT and/or HNC proteins of the present invention or computer structures of HMT and/or HNC protein's natural substrates. Preferred sites to model include one or more of the active sites of IMT and/or HNC protein. Substrate analogs can also be obtained by generating random samples of molecules, such as oligonucleotides, peptides, peptidomimetic compounds, or other inorganic or organic molecules, and screening such samples for their ability to interfere with interaction between HMT and/or HNC proteins and their substrates, e.g. by affinity chromatography techniques. A preferred HMT and/or HNC protein substrate analog is a HMT and/or HNC protein mimetic compound, i.e., a compound that is structurally and/or functionally similar to a natural substrate of a HMT and/or HNC protein of the present invention, particularly to the region of the substrate that interacts with the HMT and/or HNC protein active site, but that inhibits HMT and/or HNC protein activity upon interacting with the HMT and/or HNC protein active site.

The present invention also includes a therapeutic composition comprising at least one protective molecule of the present invention in combination with at least one additional compound protective against one or more infectious agents.

In one embodiment, a therapeutic composition of the present invention can be used to protect an animal from flea infestation by administering such composition to a flea in order to prevent infestation. Such administration to the flea and/or animal could be oral, or by application to the animal's body surface (e.g. topical spot-on, or spraying onto the animal), or by application to the environment (e.g., spraying). Examples of such compositions include, but are not limited to, transgenic vectors capable of producing at least one therapeutic composition of the present invention. In another embodiment a flea can ingest therapeutic compositions, or products thereof, present on the surface of or in the blood of a host animal that has been administered a therapeutic composition of the present invention.

In accordance with the present invention, a host animal (i.e., an animal that is or is capable of being infested with fleas) is treated by administering to the animal a therapeutic composition of the present invention in such a manner that the composition itself (e.g., a HMT and/or HNC protein, a HMT and/or HNC nucleic acid molecule, a HMT and/or HNC protein inhibitor, a HMT and/or HNC protein synthesis suppressor (i.e., a compound that decreases the production or half-life of a HMT and/or HNC protein in fleas), a HMT and/or HNC protein mimetope, or a anti-HMT and/or HNC antibody) or a product generated by the animal in response to administration of the composition (e.g., antibodies produced in response to administration of a flea HMT and/or HNC protein or nucleic acid molecule, or conversion of an inactive inhibitor "prodrug" to an active HMT and/or HNC protein inhibitor) ultimately enters the flea, A host animal is preferably treated in such a way that the compound or product thereof is present on the body surface of the animal or enters the blood stream of the animal. Fleas are then exposed to the composition or product when they feed from the animal. For example, flea HMT and/or HNC protein inhibitors administered to an animal are administered in such a way that the inhibitors enter the blood stream of the animal, where they can be taken up by feeding fleas.

The present invention also includes the ability to reduce larval flea infestation in that when fleas feed from a host animal that has been administered a therapeutic composition of the present invention, at least a portion of compounds of the present invention, or products thereof, in the blood taken up by the fleas are excreted by the fleas in feces, which is subsequently ingested by flea larvae. In particular, it is of note that flea larvae obtain most, if not all, of their nutrition from flea feces.

In accordance with the present invention, reducing HMT and/or HNC protein activity in a flea can lead to a number of outcomes that reduce flea burden on treated animals and their surrounding environments. Such outcomes include, but are not limited to, (a) reducing the viability of fleas that feed from the treated animal, (b) reducing the fecundity of female fleas that feed from the treated animal, (c) reducing the reproductive capacity of male fleas that feed from the treated animal, (d) reducing the viability of eggs laid by female fleas that feed from the treated animal, (e) altering the blood feeding behavior of fleas that feed from the treated animal (e.g., fleas take up less volume per feeding or feed less frequently), (f) reducing the viability of flea larvae, for example due to the feeding of larvae from feces of fleas that feed from the treated animal, (g) altering the development of flea larvae (e.g., by decreasing feeding behavior, inhibiting growth, inhibiting (e.g., slowing or blocking) molting, and/or otherwise inhibiting maturation to adults), and/or (h) altering or decreasing the ability of fleas or flea larvae to digest a blood meal.

In order to protect an animal from flea infestation, a therapeutic composition of the present invention is administered to the animal in an effective manner such that the composition is capable of protecting that animal from flea infestation. Therapeutic compositions of the present invention can be administered to animals prior to infestation in order to prevent infestation (i.e., as a preventative vaccine) and/or can be administered to animals after infestation. For example, proteins, mimetopes thereof, and antibodies thereof can be used as immunotherapeutic agents.

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), Flt-3 ligand, granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MEW-1 beta), and *Leishmania* elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunters Titer-rnax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, lipospheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from flea infestation. The therapeutic composition is preferably released over a period of time ranging from about 1 to about 12 months. A controlled release formulation of the present invention is capable of effecting a treatment preferably for at least 1 month, preferably for at least 3 months, preferably for at least 6 months, preferably for at least 9 months, and preferably for at least 12 months.

Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition, including a recombinant protein vaccine, is from about 1 microgram (μg) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 μg to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal, intraocular, intranasal, conjunctival, and intramuscular routes. Methods of administration for other therapeutic compounds can be determined by one skilled in the art, and may include administration of a therapeutic composition one or more times, on a daily, weekly, monthly or yearly regimen; routes of administration can be determined by one skilled in the art, and may include any route. A preferred route of administration of an inhibitory compound when administering to fleas is a topical, or "spot-on" formulation administered to the body surface of the animal, so that a flea would encounter the inhibitory compound when attached to the animal; another preferred route of administration of an inhibitory compound is an oral formulation that, when fed to an animal, would enter the bloodstream of the animal, which would then be transferred to a flea while feeding from the animal.

A recombinant protein vaccine of the present invention comprises a recombinantly-produced flea HMT and/or HNC protein of the present invention that is administered to an animal according to a protocol that results in the animal producing a sufficient immune response to protect itself from a flea infestation. Such protocols can be determined by those skilled in the art.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, *Science* 247, 1465-1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome, i.e., a viral vector. Preferred viral vectors include those based on alphaviruses, poxviruses, adenoviruses, herpesviruses, picornaviruses, and retroviruses, with those based on alphaviruses, such as sindbis or Semliki forest virus, species-specific herpesviruses and poxviruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, conjunctival, intraocular, intranasal and oral routes of administration being preferred. A preferred single dose of a genetic vaccine ranges from about 1 nanogram (ng) to about 600 μg, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxviruses, adenoviruses, herpesviruses, picornaviruses, and retroviruses. Preferred recombinant virus vaccines are those based on alphaviruses (such as Sindbis virus), raccoon poxviruses, species-specific herpesviruses and species-specific poxviruses. An example of methods to produce and use alphavirus recombinant virus vaccines are disclosed in U.S. Pat. No. 5,766,602 to Xiong and Grieve, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from flea infestation as disclosed herein. For example, a recombinant virus vaccine comprising a flea HMT and/or HNC nucleic acid molecule of the present invention is administered according to a protocol that results in the animal producing a sufficient immune response to protect itself from flea infestation. A preferred single dose of a recombinant virus vaccine of the present invention is from about $1\times10^4$ to about $1\times10^8$ virus plaque forming units (pfu) per kilogram body weight of the animal. Administration protocols are similar to those described herein for protein-based vaccines, with subcutaneous, intramuscular, intranasal, intraocular, conjunctival, and oral administration routes being preferred.

A recombinant cell vaccine of the present invention includes recombinant cells of the present invention that express at least one protein of the present invention. Preferred recombinant cells for this embodiment include *Salmonella*, *E. coli*, *Listeria*, *Mycobacteriuni*, *S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from flea infestation can be tested in a variety of ways including, but not limited to, detection of protective antibodies (using, for example, proteins or mimetopes of the present invention), detection of cellular immunity within the treated animal, or challenge of the treated animal with the fleas to determine whether the treated animal is resistant to infestation. Challenge studies can include direct administration of fleas to the treated animal. In one embodiment, therapeutic compositions can be tested in animal models such as mice. Such techniques are known to those skilled in the art.

One therapeutic composition of the present invention includes an inhibitor of flea HMT and/or HNC protein activity, i.e., a compound capable of substantially interfering with the function of a flea HMT and/or HNC protein susceptible to inhibition by an inhibitor of flea HMT and/or HNC protein activity. An inhibitor of HMT and/or HNC protein activity can be identified using flea HMT and/or HNC proteins of the present invention. An inhibitor of HMT and/or HNC protein function can be identified using flea HMT and/or HNC proteins of the present invention. A preferred inhibitor of HMT and/or HNC protein function is a compound capable of substantially interfering with the function of a flea HMT and/or HNC protein and which does not substantially interfere with host animal proteins. As used herein, a compound that does not substantially inhibit or interfere with host animal proteins is one that, when administered to a host animal, the host animal shows no significant adverse effects attributable to the compound and which, when administered to an animal in an effective manner, is capable of protecting that animal from flea infestation.

One embodiment of the present invention is a method to identify a compound capable of inhibiting HMT and/or HNC protein activity of a flea. Such a method includes the steps of (a) contacting (e.g., combining, mixing) an isolated flea HMT and/or HNC protein, preferably a *C. felis* HMT and/or HNC protein of the present invention, with a putative inhibitory compound under conditions in which, in the absence of the compound, the protein has HMT and/or HNC protein activity, and (b) determining if the putative inhibitory compound inhibits the activity. HMT and/or HNC protein activity can be determined in a variety of ways known in the art, including but not limited to determining the ability of HMT and/or HNC protein to bind to or otherwise interact with a substrate. Such conditions under which a HMT and/or HNC protein has HMT and/or HNC protein activity include conditions in which a HMT and/or HNC protein has a correct three-dimensionally folded structure under physiologic conditions, i.e. physiologic pH, physiologic ionic concentrations, and physiologic temperatures.

Putative inhibitory compounds to screen include antibodies (including fragments and mimetopes thereof), putative substrate analogs, and other, preferably small, organic or inorganic molecules. Methods to determine HMT and/or HNC protein activity are known to those skilled in the art; see, for example, the Examples section of the present application. Methods to determine binding of a putative inhibitory compound to a HMT and/or HNC protein of the present invention are known to those of skill in the art and include, for example, determining changes in molecular mass using surface plasmon resonance (e.g., determining light scatter by an inhibitor of a HMT and/or HNC protein, before and after contacting the inhibitor or protein with a HMT and/or HNC protein or inhibitor, respectively) or screening for compounds that inhibit interaction between a HMT and/or HNC protein and a substrate.

A preferred method to identify a compound capable of inhibiting HMT and/or HNC protein activity includes contacting an isolated flea HMT and/or HNC protein encoded by a nucleic acid molecule of Table I and/or Table II; (b) a protein comprising an at least 25 consecutive amino acid portion identical in sequence to a consecutive amino acid portion of a sequence as set forth in (a), wherein the protein has HMT and/or HNC protein activity; (c) a protein comprising a fragment of a protein as set forth in (a), wherein the fragment has an activity selected from the group consisting of binding to a HMT and/or HNC molecule and hydrolyzing a HMT and/or HNC protein substrate; and (d) a protein encoded by an allelic variant of a nucleic acid molecule that encodes any protein of (a), (b), or (c), with a putative inhibitory compound under conditions in which, in the absence of the compound, the protein has HMT and/or HNC protein activity; and determining if the putative inhibitory compound inhibits the activity.

Another embodiment of the present invention is an assay kit to identify an inhibitor of a flea HMT and/or HNC protein of the present invention. This kit comprises an isolated flea HMT and/or HNC protein of the present invention, and a means for determining inhibition of an activity of flea HMT and/or HNC protein, where the means enables detection of inhibition. Detection of inhibition of flea HMT and/or HNC protein identifies a putative inhibitor to be an inhibitor of flea HMT and/or HNC protein. Means for determining inhibition of flea HMT and/or HNC protein include an assay system that detects binding of a putative inhibitor to a flea HMT and/or HNC molecule, and an assay system that detects interference by a putative inhibitor of the ability of flea HMT and/or HNC protein to hydrolyze a substrate. Means and methods are described herein and are known to those skilled in the art.

The following examples are provided for the purposes of illustration and are not intended to limit the scope of the present invention. The following examples include a number of recombinant DNA and protein chemistry techniques known to those skilled in the art; see, for example, Sambrook et al., ibid.

EXAMPLE 1

This Example describes the isolation of RNA from the hindgut and Malpighian tubules (HMT) of *Ctenocephalides felis* and the use of isolated RNA to construct to subtracted and unsubtracted EDNA libraries.

Approximately 10,000 hindguts and Malpighian tubules were dissected from equal numbers of cat blood fed and unfed adult *C. felis* with a male to female ratio of 1 to 4, and total RNA was extracted using a guanidine isothiocyanate lysis buffer and the standard procedure described by Sambrook et al. Poly-A enriched mRNA was purified from total RNA above using a mRNA Purification Kit, available from Pharmacia Biotech, Piscataway, N.J., following the manufacturer's protocol. The same procedures were used to extract total RNA and isolate poly-A enriched mRNA from the dissected *C. felis* bodies following removal of HMT, referred to hereinafter as "non-HMT mRNA".

Poly-A enriched mRNA was used to construct a cDNA library using subtractive hybridization and suppression PCR as follows. Subtractive hybridization and suppression PCR was conducted using a PCR-Select™ cDNA Subtraction Kit, available from Clontech Laboratories, Inc., Palo Alto, Calif. according to the manufacturer's instructions. Briefly, this kit uses subtractive hybridization and suppression PCR to specifically amplify cDNA sequences that are present in the tester cDNA and absent in the driver cDNA, thus enriching for tester-specific sequences. The efficiency of the subtraction process can be assessed by semi-quantitative PCR and by comparing the ethidium bromide staining patterns of the subtracted and unsubtracted samples on agarose gels as described in section V.D. of the manufacturer's protocol. For the semi-quantitative PCR, three genes with mRNAs known to be expressed outside of the HMT tissue were used to test for specific subtraction. These genes encoded putative actin, N-aminopeptidase, and serine protease proteins.

Subtractive hybridization and suppression PCR was conducted under the following conditions. Two micrograms (µg) of HMT mRNA was used as the template for synthesis of the tester material and 2 µg of non-HMT mRNA was used as template for synthesis of the driver material in this reaction. The number of cycles used in the selective amplification steps was optimized using the manufacturer's protocols. Optimization resulted in the use of 24 rather than the standard 27 cycles of primary PCR in combination with 15 cycles of secondary PCR rather than the standard 12 cycles.

The products from the suppressive PCR reaction were ligated into the pCR®2.1 vector, available from Invitrogen, Carlsbad, Calif., using an Original TA Cloning® Kit, available from Invitrogen. The ligation reaction was then used to transform INVαF' One Shot™ competent cells, available from Invitrogen, which were plated on Luria broth (LB) agar with 50 micrograms per milliliter (µg/ml) ampicillin, available from Sigma-Aldrich Co., St. Louis, Mo., and 50 µg/ml 5-bromo-4-chloro-3-indoyl β-D-galactopyranoside (X-Gal), available from Fisher Biotech, Fair Lawn, N.J. Transformed colonies were amplified and the DNA isolated using the standard alkaline lysis procedure described by Sambrook et al., ibid.

Automated cycle sequencing of DNA samples was performed using an ABI PRISM™ Model 377, available from Perkins Elmer, with XL upgrade DNA Sequencer, available from PE Applied Biosystems, Foster City, Calif., after reactions were carried out using the PRISM™ Dye Terminator Cycle Sequencing Ready Reaction Kit or the PRISM™ dRhodamine Terminator Cycle Sequencing Ready Reaction Kit or the PRISM™ BigDye™ Terminator Cycle sequencing Ready Reaction Kit, available from PE Applied Biosystems, following the manufacturer's protocol, hereinafter "standard sequencing methods". The resulting sequences are presented in Table II. Sequence analysis was performed using the MacVector™ sequence analysis software, available from International Biotechnologies Inc., New Haven, Conn., and the SeqLab sequence analysis software, using default parameters. Each sequence read was trimmed of vector sequence at either end and submitted for a search through the National Center for Biotechnology Information (NCBI), National Library of Medicine, National Institute of Health, Baltimore, Md., using the BLAST network. This database includes SwisProt+PIR+SPupdate+GenPept+GPUpdate+PDB databases. The search was conducted using the xBLAST function, which compares the translated sequences in all 6 reading frames to the protein sequences contained in the database.

An unsubtracted HMT cDNA library was constructed as follows. Approximately 10,000 HMT tissues were dissected from equal numbers of unfed and cat blood-fed adult *C. felis* with a male to female ratio of 1:4. Total KNA was extracted using a guanidine isothiocyanate lysis buffer and procedures described in Sambrook et al., followed by isolation using a mRNA purification kit, available from Pharmacia, according to the manufacturer's protocols. The library was constructed with 5 µg of isolated mRNA using a ZAP-cDNA® cDNA synthesis kit, and packaged using a ZAP-cDNA® Gigapack® gold cloning kit, both available from Stratagene, La Jolla, Calif. The resultant HMT library was amplified to a titer of about 5×10$^9$ plaque forming units per milliliter (pfu/ml). Single clone excisions were performed using the Ex-Assist™ helper phage, available from Stratagene, and used to create double stranded plasmid template for sequencing using the manufacturer's protocols with the following exceptions. Following incubation of the SOLR cells with the cleared phage lysate, the mixture was used to inoculate LB broth, and the mix was incubated overnight and then subjected to mini-prep plasmid preparation and sequencing as described for the subtracted HMT library above.

EXAMPLE 2

This Example describes the isolation of RNA from the head and nerve cord (HNC) of *Ctenocephalides felis* and the use of isolated RNA to construct subtracted and unsubtracted cDNA libraries.

Approximately 4,000 heads and attached nerve cords, including the terminal abdominal ganglia were dissected from equal numbers of cat blood-fed and unfed adult C. felis with a male to female ratio of 1 to 4, and total RNA was extracted using a guanidine isothiocyanate lysis buffer and the standard procedure described by Sambrook et al. Approximately 618 µg of total RNA was recovered. Poly-A enriched mRNA was purified from total RNA above using a mRNA Purification Kit, available from Pharmacia, following the manufacturer's protocol. Approximately 13 µg of mRNA was isolated. The same procedures were used to extract total RNA and isolate poly-A enriched mRNA from the dissected C. felis bodies following removal of HNC tissues, referred to hereinafter as "non-HNC mRNA".

Suppression subtractive PCR was conducted as described in Example 1 using a PCR-Select™ cDNA Subtraction kit, available from Clontech, under the following conditions. Two micrograms (µg) of HNC mRNA was used as the template for synthesis of the tester material and 2 µg of non-HMT mRNA was used as template for synthesis of the driver material in this reaction. The number of cycles used in the selective amplification steps was optimized using the manufacturer's protocols. Optimization resulted in the use of 24 rather than the standard 27 cycles of primary PCR in combination with either 12 or 15 cycles of secondary PCR.

cDNA pools from various PCR cycling combinations were ligated into the TA vector using a TA cloning kit, available from Invitrogen. Aliquots of ligation reaction were transformed into Ultramax DH5α™ bacteria, available from Gibco-BRL, Gaithersburg, Md. Portions of the transformation mixes were used to inoculate LB broth cultures containing 100 µg/ml of ampicillin. The overnight cultures were plated to generate discreet colonies which were used individually for overnight cultures for plasmid preps. Transformed colonies were amplified and the DNA isolated using the standard alkaline lysis procedure described by Sambrook et al., ibid.

Automated cycle sequencing of DNA samples was performed using the standard sequencing methods described in Example 1. The resulting sequences are presented in Table I. Sequence analysis was performed using the MacVector™ sequence analysis software, available from International Biotechnologies Inc., New Haven, Conn., and the SeqLab sequence analysis software, using default parameters.

An unsubtracted EDNA library was constructed as follows. Approximately 6400 head and nerve cords were dissected from C. felis and poly-A RNA was isolated as described above. About seven µg of HNC poly-A RNA was used to construct a cDNA library using Stratagene's λZAP-cDNA Synthesis Kit and protocol. The resultant HNC library was amplified to a titer of about $5 \times 10^9$ plaque forming units per milliliter (pfu/ml). Single clone excisions were performed using the Ex-Assist helper phage, available from Stratagene, and used to create double stranded plasmid template for sequencing using the manufacturer's protocols with the following exceptions. Following incubation of the SOLR cells with the cleared phage lysate, the mixture was used to inoculate LB broth, and the mix was incubated overnight and then subjected to mini-prep plasmid preparation and sequencing as described for the subtracted library above.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08088903B2). An electronic copy of the "Sequence Listing" will also be available from the USPTO upon request and payment of the fee set forth in 37 CFR 1.19(b)(3).

What is claimed is:

1. An isolated nucleic acid molecule comprising a nucleic acid sequence selected from the group consisting of:
   a. a nucleic acid sequence selected from the group consisting of SEQ ID NO:23, SEQ ID NO:26, SEQ ID NO:230 and SEQ ID NO:2107, and;
   b. a nucleic acid sequence fully complementary to the nucleic acid sequence of (a).

2. An isolated nucleic acid molecule selected from the group consisting of:
   a. a nucleic acid molecule consisting of at least 200 contiguous nucleotides from SEQ ID NO: 23, SEQ ID NO:26, or SEQ ID NO:230;
   b. a nucleic acid molecule consisting of at least 375 contiguous nucleotides from SEQ ID NO:2107; and
   c. a nucleic acid sequence fully complementary to the nucleic acid sequence of (a) or (b).

3. The isolated nucleic acid molecule of claim 2, wherein said nucleic acid molecule consists of a nucleic acid sequence selected from the group consisting of:
   a. a nucleic acid sequence selected from the group consisting of SEQ ID NO:23, SEQ ID NO:26, SEQ ID NO:230 and SEQ ID NO:2107, and;
   b. a nucleic acid sequence fully complementary to the nucleic acid sequence of (a).

* * * * *